(12) United States Patent
Freyne et al.

(10) Patent No.: US 8,168,644 B2
(45) Date of Patent: May 1, 2012

(54) QUINAZOLINONE DERIVATIVES AS TUBULIN POLYMERIZATION INHIBITORS

(75) Inventors: Eddy Jean Edgard Freyne, Rumst (BE); Laurence Anne Mevellec, Louviers (FR); Jorge Eduardo Vialard, Brussels (BE); Christophe Meyer, Les Authieux sur le Port Saint Ouen (FR); Elisabeth Thérèse Jeanne Pasquier, Val de Reuil (FR); Xavier Marc Bourdrez, Saint Pierre du Vauvray (FR); Patrick René Angibaud, Fontaine-Bellenger (FR)

(73) Assignee: Janssen Pharmaceutica NV, Beerse (BE)

( * ) Notice: Subject to any disclaimer, the term of this patent is extended or adjusted under 35 U.S.C. 154(b) by 0 days.

(21) Appl. No.: 12/934,733

(22) PCT Filed: Mar. 26, 2009

(86) PCT No.: PCT/EP2009/053604
§ 371 (c)(1),
(2), (4) Date: Sep. 27, 2010

(87) PCT Pub. No.: WO2009/118384
PCT Pub. Date: Oct. 1, 2009

(65) Prior Publication Data
US 2011/0028433 A1 Feb. 3, 2011

(30) Foreign Application Priority Data
Mar. 27, 2008 (EP) .................................. 08153428

(51) Int. Cl.
*A01N 43/54* (2006.01)
*A61K 31/517* (2006.01)
*C07D 239/72* (2006.01)
(52) U.S. Cl. ..................... 514/266.1; 544/283
(58) Field of Classification Search ............... 514/266.1; 544/283
See application file for complete search history.

(56) References Cited

U.S. PATENT DOCUMENTS

| | | | |
|---|---|---|---|
| 3,274,194 | A | 9/1966 | Hayao et al. |
| 3,753,988 | A | 8/1973 | Rodway et al. |
| 3,919,425 | A | 11/1975 | Vidrio |
| 4,335,127 | A | 6/1982 | Vandenberk et al. |
| 5,028,606 | A | 7/1991 | Venet et al. |
| 5,118,684 | A | 6/1992 | Sugimoto et al. |
| 5,151,421 | A | 9/1992 | Venet et al. |
| 5,177,075 | A | 1/1993 | Suto et al. |
| 5,231,184 | A | 7/1993 | Stokbroekx et al. |
| 5,304,560 | A | 4/1994 | Shimazaki et al. |
| 5,374,637 | A | 12/1994 | Van Daele et al. |
| 6,583,144 | B2 | 6/2003 | Ohkura et al. |
| 6,635,642 | B1 | 10/2003 | Jackson et al. |
| 7,115,630 | B2 | 10/2006 | Mabire et al. |
| 2002/0002174 | A1 | 1/2002 | Nieduzak et al. |
| 2003/0130505 | A1 | 7/2003 | Zhi et al. |
| 2003/0225268 | A1 | 12/2003 | Bunnelle et al. |
| 2004/0077667 | A1 | 4/2004 | Matsuoka et al. |
| 2004/0176361 | A1 | 9/2004 | Fujio et al. |
| 2008/0039480 | A1 | 2/2008 | Kennis et al. |
| 2008/0269234 | A1 | 10/2008 | Gandhi et al. |
| 2009/0048259 | A1 | 2/2009 | Austin et al. |
| 2009/0292121 | A1 | 11/2009 | Morioka et al. |

FOREIGN PATENT DOCUMENTS

| | | |
|---|---|---|
| DE | 1006423 | 4/1957 |
| DE | 2258561 A | 6/1973 |
| EP | 0013612 | 11/1983 |
| EP | 156433 | 10/1985 |
| EP | 391462 | 10/1990 |
| EP | 0638567 | 2/1995 |
| EP | 0371564 | 7/1995 |
| EP | 0669919 | 9/1995 |
| EP | 1026160 A1 | 8/2000 |
| EP | 0885190 | 5/2003 |
| EP | 1355888 | 10/2008 |
| FR | 2436781 | 5/1980 |
| GB | 732581 A | 6/1955 |
| GB | 1062357 | 3/1967 |
| JP | 59-076082 | 4/1984 |
| JP | 60-120872 | 6/1985 |
| JP | 60-226862 | 11/1985 |
| JP | 62-234065 | 10/1987 |
| JP | 10007572 | 1/1998 |
| JP | 10-330377 | 12/1998 |
| JP | 2002-515072 | 3/1999 |

(Continued)

OTHER PUBLICATIONS

Vippagunta et al., "Crystalline solids", Adv. Drug Delivery Reviews 48 (2001) 3-26.*
Bonne, D., et al., "4'6-Diamidino-2-phenylindole, a Fluorescent Probe for Tubulin and Microtubules*", Journal of Biological Chemistry, vol. 260, No. 5 (1985) pp. 2819-2825.
Tentori, L., et al. "Poly(ADP-ribose)polymerase (PARP) Inhibition or PARP-1 gene Deletion Reduces Angiogenesis", European Journal of Cancer, vol. 43, No. 14 (2007) pp. 2124-2133.
International Search Report for corresponding Application No. PCT/EP2009/053604 mailed May 8, 2009.
Albert, J.M., et al., "Inhibition of Poly(ADP-Ribose) Polyerase Enhances Cell Death and Improves Tumor Growth Delay in Irradiated Lung Cancer MODels", Clin Cancer Res, (2007), vol. 13, No. 10, pp. 3033-3042 (cited by Examiner Jan. 21, 2009).

(Continued)

*Primary Examiner* — Paul V. Ward

(57) ABSTRACT

The present invention provides compounds of formula (I), their use as inhibitors of tubulin polymerization as well as pharmaceutical compositions comprising said compounds of formula (I)

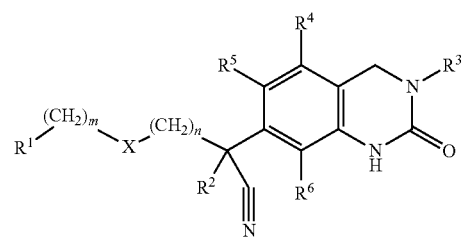

wherein $R^1$, $R^2$, $R^3$, $R^4$, $R^5$, $R^6$, n, m and X have defined meanings.

7 Claims, No Drawings

FOREIGN PATENT DOCUMENTS

| | | |
|---|---|---|
| JP | 2000-505100 | 4/2000 |
| JP | 2000191659 | 7/2000 |
| JP | 2002-535409 | 8/2000 |
| JP | 2002284699 | 10/2002 |
| WO | WO 91/12006 A2 | 8/1991 |
| WO | WO 9322309 A1 | 11/1993 |
| WO | WO 94/19342 A1 | 9/1994 |
| WO | WO 95/24379 A1 | 9/1995 |
| WO | WO 98/11128 A1 | 3/1998 |
| WO | WO 99/11649 A2 | 3/1999 |
| WO | WO 99/29687 A1 | 6/1999 |
| WO | WO 00/44755 A1 | 8/2000 |
| WO | WO 02/28837 A1 | 4/2002 |
| WO | WO 02/36599 A1 | 5/2002 |
| WO | WO 02/48117 A1 | 6/2002 |
| WO | WO 03/015785 A1 | 2/2003 |
| WO | WO 03/039460 A2 | 5/2003 |
| WO | WO 03/055865 A1 | 7/2003 |
| WO | WO 03/080581 A1 | 10/2003 |
| WO | WO 03/082350 A2 | 10/2003 |
| WO | WO 03/101985 | 12/2003 |
| WO | WO 03/101985 A1 | 12/2003 |
| WO | WO 2005/004801 A2 | 1/2005 |
| WO | WO 2005/054199 A1 | 6/2005 |
| WO | WO 2005/054201 A1 | 6/2005 |
| WO | WO 2005/054209 A1 | 6/2005 |
| WO | WO 2005/054210 A1 | 6/2005 |
| WO | WO 2005/058843 A1 | 6/2005 |
| WO | WO 2005/097750 A1 | 10/2005 |
| WO | WO 2005/117876 A1 | 12/2005 |
| WO | WO 2006/003146 A1 | 1/2006 |
| WO | WO 2006/003147 A1 | 1/2006 |
| WO | WO 2006/003148 A1 | 1/2006 |
| WO | WO 2006/003150 A1 | 1/2006 |
| WO | WO 2006/089177 A2 | 8/2006 |
| WO | WO 2007/025009 A2 | 3/2007 |
| WO | WO 2007/087684 A1 | 8/2007 |
| WO | WO 2007/095628 A1 | 8/2007 |
| WO | WO 2008/107478 A1 | 9/2008 |
| ZA | 72/8536 A | 11/1972 |

OTHER PUBLICATIONS

Ali, M.M., et al., "Synthesis and Antimicrobial Activities of Some Novel Quinoxalinone Derivatives", Molecules, (2000), vol. 5, No. 6, pp. 864-873.

Ame, J.C., et al., "PARP-2, a Novel Mammalian DNA Damage-Dependent Poly(ADP-Ribose) Polymerase", Journal of Biological Chemistry, (1999), vol. 274, No. 25, pp. 17860-17868.

Ame, J.C., et al., "The PARP Superfamily", BioEssays, (2004), vol. 26, No. 8, pp. 882-893.

Bellasio, E., et al., "Antihypertensives. N-1H-Pyrrol-1-YL-3-Pyridazinamines", J. Med. Chem., (1984), vol. 27, No. 8 pp. 1077-1083.

Blackburn, W., et al., "The Preparation of 3-Methyl-6- and -7-Carboxy-2-Quinoxalones", Journal of Organic Chemistry, ((1961), vol. 26, pp. 2805-2809 (cited by Examiner May 15, 2008).

Bloch, W., et al., "Poly-Adenosine Diphosphate-Ribose Polymerase Inhibition for Myocardial Protection: Pathopysiologic and Physiologic Considerations", Journal of Thoracic and Cardiovascular Surgery, vol. 128, No. 2, pp. 323-324 (cited by Examiner Aug. 4, 2008).

Bonne, D., et al., "4',6-Diamidino-2-Phenylindole, a Fluorescent Probe for Tubulin and Microtubules", Journal f Biological Chemistry, (1985), vol. 260, No. 5, pp. 2819-2825.

Calabrese, C.R., et al., "Anticancer Chemosensitization and Radiosensitization by the Novel Poly(ADP-Ribose) Polymerase-1 Inhibitor AG14361", Journal of the National Cancer Institute, (2004), vol. 96, No. 1, pp. 56-67 (cited by Examiner Aug. 20, 2010).

Cardozo, M.G., et al., "Conformational Analyses and Molecular-Shape Comparisons of a Series of Indanone-Benzylpiperidine Inhibitors of Acetylcholinesterase", J. Med. Chem., (1992), vol. 35, pp. 590-601.

Cockcroft, X., et al., "Phthalazines 2: Optimisation and Synthesis of Novel Potent Inhibitors of Poly(ADP-Ribose)Polymerase", Bioorganic & Medicinal Chemistry Letters, (2006), vol. 16, pp. 1040-1044 (cited by Examiner Aug. 4, 2008).

Costantino, G., et al., "Modeling of Poly(ADP-Ribose)Polymerase (PARP) Inhibitors. Docking of Ligands and Quantitative Structure-Activity Relationship Analysis", J. Med. Chem., (2001), vol. 44, pp. 3786-3794.

Cuzzocrea, S., "Shock Inflammation and PARP", Pharmacological Research, (2005), vol. 52, pp. 72-82 (cited by Examiner Aug. 4, 2008).

Dastmalchi, S., et al., "Molecular Modelling of Human Aldehyde Oxidase and Identification of the Key Interactions in the Enzyme-Substrate Complex", Daru, J. Faculty of Pharm., (2005), vol. 13, No. 3, pp. 82-93 (cited by Examiner Aug. 19, 2011).

Dörwald, F.Z., "Side Reactions in Organic Synthesis": A Guide to Successful Synthesis Design, Weinheim: WILEY-VCH Verlag GmbH & Co. KGaA, (2005), Preface (cited by Examiner Jan. 26, 2009).

Golbraikh, A., et al., "Validation of Protein-Based Alignment in 3D Quantitative Structure-Activity Relationships With CoMFA Models", Eur. J. Med. Chem., (2000), vol. 35, pp. 123-136.

Guery, S., et al., "Synthesis of 4-ARYL-1-(4-Methylpiperazin-1-Yl)Phthalazines by Suzuki-Type Cross-Coupling Reaction", Synthesis, (2001), No. 5, pp. 699-701.

Gupta, C.M., et al., "Drugs Acting on the Central Nervous System. Syntheses of Substituted Quinazolones and Quinazolines and Triazepino- and Triazocinoquinazolones", Journal of Medicinal Chemistry (1968), vol. 11, No. 2, pp. 392-395.

Habon, T., et al., "The Effect of Carvedilol on Enhanced ADP-Ribosylation and Red Blood Cell Membrane Damage Caused by Free Radicals", Cardiovascular Research, (2001), vol. 52, p. 153-160 (cited by Examiner Mar. 24, 2009).

Hayao, S., et al., "New Sedative and Hypotensive 3-Substituted 2,4(1H,3h-)-Quinazolinediones", Journal of Medicinal Chemistry, (1965), vol. 8, pp. 807-811.

Hazard, P.R., et al., "De Quelques Actions Pharmacologiques Exercees Par des Derives de l'Orthoprocainamide", Thérapie, (1965), vol. XX, pp. 1043-1049 (cited by Examiner Aug. 20, 2010).

Herndon, J.L., et al., "Ketanserin Analogues: Structure-Affinity Relationships for 5-HT$_2$ and 5-HT$_{1C}$ Serotonin Receptor Binding", J. Med. Chem., (1992), vol. 35, pp. 4903-4910 (cited by Examiner Aug. 20, 2010).

Hori, M., et al., "Novel 4-Phenoxy-2-(1-Piperazinyl)Quinazolines as Potent Anticonvulsive and Antihypdxic Agents", Chem. Pharm. Bull, (1990), vol. 38, No. 3, pp. 681-687.

Hori, M., et al., "Novel 4-Phenoxy-2-(1-Piperazinyl)Quinazolines as Potent Anticonvulsive and Antihypdxic Agents", Chem. Pharm. Bull, (1990), vol. 38, No. 5, pp. 1286-1291.

Horvath, E.M., et al., "Poly(ADP-Ribose) Polymerase as a Drug Target for Cardiovascular Disease and Cancer: An Update", Drug News Perspect, (2007), vol. 20, No. 3, pp. 171-181.

Jordan, V.C., "Tamoxifen: A Most Unlikely Pioneering Medicine", Nature Reviews, (2003), vol. 2, pp. 205-213 (cited by Examiner Jan. 26, 2009).

Katoh, A., et al., "Synthesis of Quinoxaline Derivatives Bearing the Styryl and Phenylethynyl Groups and Application to a Fluorescence Derivatization Reagent", Heterocycles, (2000), vol. 52, No. 2, pp. 911-920 (cited by Examiner May 15, 2008).

Kormendy, K., et al., "Aminophthalazinone Derivatives, V Synthesis of 4-Hydrazino-1-(2-H)0phthalazinones, I", Acta Chimica Academiae Scientiarum Hungaricae, (1979), vol. 102, No. 1, pp. 39-50 (cited by Examiner Aug. 4, 2008).

Kornet, M.J., et al., "Synthesis of 3-Amino-2,4(1H,3H)-Quinazolinediones for Testing as Anticonvulsants", J. Heterocyclic Chem., (1984), vol. 21, No. 5, pp. 1533-1535 (cited by Examiner Aug. 20, 2010).

Kulcsar, G., et al., Synthesis and Study of New 4-Quinazolinone Inhibitors of the DNA Repair Enzyme Poly(ADP-Ribose) Polymerase (PARP), Arkivoc, XX,XX, (2003), vol. 2003, No. Part V, pp. 121-131.

Larner, A.J., "Poly(ADP-Ribose) Polymerase Inhibitors in the Prevention of Neuronal Cell Death", Expert Opin. Ther. Patents, (2002), vol. 12, No. 4, pp. 481-487 (cited by Examiner Apr. 2, 2009).

Li, J.H., et al., "PARP Inhibitors", IDrugs, (2001), vol. 4, No. 7, pp. 804-812.

Lord, C.J., et al., "Targeted Therapy for Cancer Using PARP Inhibitors", Current Opinion in Pharmacology, (2008), vol. 8, pp. 363-369 (cited by Examiner Apr. 2, 2009).

Meier, H.L., et al., "Alterations in Human Lymphocyte DNA Caused by Sulfur Mustard Can Be Mitigated by Selective Inhibitors of Poly(ADP-Ribose) Polymerase", Biochimica et Biophysica Acta, (1998), vol. 1404, pp. 367-376 (cited by Examiner Mar. 24, 2009).

Miller, B.A., "Inhibition of TRPM2 Function by PARP Inhibitors Protects Cells From Oxidative Stress-Induced Death", British Journal of Pharmacology, (2004), vol. 143, pp. 515-516 (cited by Examiner Aug. 4, 2008).

Nguewa, P.A., et al., "Poly(ADP-Ribose) Polymerases: Homology, Structural Domains and Functions. Novel Therapeutical Applications", Progress in Biophysics & Molecular Biology, (2005), vol. 88, pp. 143-172.

Oliver, A.W., et al., "Crystal Structure of the Catalytic Fragment of Murine Poly(ADP-Ribose) Polymerase-2", Nucleic Acids Research, (2004), vol. 32, No. 4, pp. 456-464.

Schreiber, V., et al., "Poly(ADP-Ribose) Polymerase-2 is Required for Efficient Base Excision DNA Repair in Association With PARP-1 and XRCC1", Journal of Biological Chemistry, (2002), vol. 277, No. 25, pp. 23028-23036.

Szabo, G., et al., "Poly(ADP-Ribose Polymerase Inhibition Protects Against Myocardial and Endothelial Reperfusion Injury After Hypothermic Cardiac Arrest", Journal of Thoracic and Cardiovascular Surgery, (2003), vol. 126, No. 3, pp. 651-658 (cited by Examiner Aug. 4, 2008).

Takai, H., et al., "Synthesis of Piperidine Derivatives With a Quinazoline Ring System as Potential Antihypertensive Agents", Chem. Pharm. Bull, (1986), vol. 34, No. 5, pp. 1907-1916 (cited by Examiner Aug. 20, 2010).

Tasatargil, A., et al., "Poly(ADP-Ribose) Polymerase Inhibition Prevents Homocysteine-Induced Endothelial Dysfunction in the Isolated Rat Aorta", Pharmacology, (2004), vol. 72, pp. 99-105 (cited by Examiner Aug. 4, 2008).

Tentori, L., et al., "Chemopotentiation by PARP Inhibitors in Cancer Therapy", Pharmacological Research, (2005), vol. 52, pp. 25-33 (cited by Examiner Jan. 21, 2009).

Vippagunta, S.R., et al., "Crystalline Solids", Advanced Drug Delivery Reviews, (2001), vol. 48, pp. 3-26 (cited by Examiner Apr. 22, 2011).

Virag, L., et al., "The Therapeutic Potential of Poly(ADP-Ribose) Polymerase Inhibitors", Pharmacological Reviews, (2002), vol. 54, No. 3, pp. 375-429 (cited by Examiner May 15, 2008).

Weltin, D., et al., "Effect of 6(5H)-Phenanthridinone, an Inhibitor of Poly(ADP-Ribose) Polymerase, on Cultured Tumor Cells", Oncology Research, (1994), vol. 6, No. 9, pp. 399-403.

Wolff, M.E., Burger's Medicinal Chemistry, $4^{th}$ ed., Part I The Basis of Medicinal Chemistry, (1980), pp. 336-337 (cited by Examiner Nov. 4, 2008).

Yolles, S., et al., "Quinoxaline Studies. I. The Preparation of 2-Hydroxy-3-Methyl-6-Methoxyquinoxaline and 2-Hydroxy-3-Methyl-7-Methoxyquinoxaline", Journal of the American Chemical Society, (1949), vol. 71, pp. 2375-2377 (cited by Examiner May 15, 2008).

Zhang, J., "PARP Inhibition: A Novel Approach to Treat Ischaemia/Reperfusion and Inflammation-Related Injuries", Emerging Drugs, (1999), vol. 4, pp. 209-221 (cited by Examiner Apr. 2, 2009).

"Cancer definition", http://www.medterms.com/script/main/art.asp?articlekey=2580, accessed Nov. 27, 2007 (cited by Examiner Aug. 20, 2010).

The Merck Index, $13^{th}$ Ed., p. 670, monograph for "Ethyl Alcohol" © 2001 by Merck and Co., Inc. (cited by Examiner May 15, 2008).

"Prostate Cancer Prevention", http://www.cancer.gov/cancertopics/pdq/prevention/prostate/Patient, accessed Apr. 9, 2010 (cited by Examiner Aug. 20, 2010).

EDAN30610, Jun. 8, 2011 (cited by Examiner Aug. 19, 2011).

Database CA 'Online! Chemical Abstracts Service, Columbus, Ohio, US; 2002, Tatsuno, Toru et al: "PARP Inhibitors for Treatment of Retinal Degeneration or Chemotherapy-Induced Cell Injury" XP002348719 retrieved from STN Database accession No. 2002:747681, relevant to claim 1-12.

Patent Abstracts of Japan, vol. 1998, No. 5, Apr. 30, 1998-& JP 10007572 A (Sumitomo Pharmaceut Co Ltd), Jan. 13, 1998 '0046!, Formula 14 abstract.

Database WPI 'Online! Derwent Publications Ltd., London, GB; XP002347462, retrieved from WPI accession No. 1970-18449R, *; see RN 27631-66-9:3-(piperidin-1-yl-propyl)-1H-quinazoline-2,4-dione*, abstract & JP 45007058B (Sankyo) Jul. 6, 1967.

Finney, D. J., "Graded Response: The Linear Dosage-Response Curve", Probit Analysis, 2nd Edition, Chapter 10 (1962), Cambridge Publishing Press, 16 page article.

International Search report for Application No. PCT/EP2004/013162 mailed Mar. 18, 2005.

International Search report for Application No. PCT/EP2004/013163 mailed Apr. 20, 2005.

International Search report for Application No. PCT/EP2004/013164 mailed Mar. 14, 2005.

International Search report for Application No. PCT/EP2004/013165 mailed Mar. 24, 2005.

International Search report for Application No. PCT/EP2005/053029 mailed Oct. 7, 2005.

International Search report for Application No. PCT/EP2005/053030 mailed Oct. 24, 2005.

International Search report for Application No. PCT/EP2005/053031 mailed Oct. 25, 2005.

International Search report for Application No. PCT/EP2008/052764 mailed Aug. 12, 2008.

International Search report for Application No. PCT/EP2008/064243 mailed Mar. 30, 2009.

International Search report for Application No. PCT/EP2009/053598 mailed May 19, 2009.

International Search report for Application No. PCT/EP2009/053604 mailed May 8, 2009.

* cited by examiner

QUINAZOLINONE DERIVATIVES AS TUBULIN POLYMERIZATION INHIBITORS

CROSS REFERENCE TO RELATED APPLICATIONS

This application is a national stage of PCT Application No. PCT/EP2009/053604, filed Mar. 26, 2009, which claims priority for EPO Patent Application No. 08153428.1, filed Mar. 27, 2008, all of which are hereby incorporated by reference in their entirety.

FIELD OF THE INVENTION

The present invention relates to inhibitors of tubulin polymerization and provides compounds and compositions containing the disclosed compounds. Moreover, the present invention provides methods of using the disclosed tubulin polymerization inhibitors for instance as a medicine.

Tubulin is composed of a heterodimer of two related proteins called α and β tubulin. Tubulin polymerizes to form structures called microtubules. Microtubules are highly dynamic cytoskeletal elements and play a critical role in many processes in eukaryotic cells, including mitosis, cell mobility, cell shape, intracellular organelle transport and cell-cell interactions.

For proper cell division to occur, it is essential that microtubules are able to polymerize and depolymerize. Microtubules in the mitotic spindle are more dynamic than those in non-dividing cells, and thus can be targeted by agents that affect microtubule dynamics. By altering microtubule polymerization/depolymerization these agents affect mitotic spindle formation, arrest dividing cells in the G2/M phase of the cell cycle, and ultimately lead to apoptotic cell death. As neoplastic cells have high proliferation rates, they can be targeted by these antimitotic agents.

Three main classes of tubulin-binding drugs, namely colchicine analogues, Vinca alkaloids and the taxanes have been identified, each of which possesses a specific binding site on the β-tubulin molecules. Paclitaxel and related taxanes represent a class of drugs that stabilizes microtubules, a process that ultimately leads to the freezing of the microtubule structures so that they can not be restructured. Subsequent arrest at mitosis induces the apoptotic mechanism to cause cell death. The second class of compounds, the colchicine analogues, as well as several other compounds, bind to the same site on β-tubulin as colchicine and disrupt polymerization and microtubular formation. The third class of compounds, vinblastine and several other vinca-related drugs, bind to the Vinca-site and prevent microtubule formation and destabilize microtubules.

Tubulin is also a target for treating disease states that are dependent or result from the abnormal formation of blood vessels (neovascularisation) such as cancerous tumours. In these cases the cytoskeleton of the vascular endothelial cells are disrupted through depolymerization of microtubules, which results from inhibiting the polymerization of tubulin to form microtubules. Microtubule length is dependent on the rate of depolymerization versus polymerization. Depolymerizing microtubules through inhibition of polymerization leads to a change in endothelial cell morphology, which than causes a blockage or shutdown in blood flow. In the case of cancerous tumours, blood flow to the diseased tissue is stopped, depriving the tumour from oxygen and nutrients leading to necrotic cell death. Neovascular systems are more sensitive to these agents because they are more dependent on microtubule cytoskeleton than normal, healthy vascular endothelial cells which are also supported by actin based cytoskeleton structures. For a number of tubulin polymerization inhibitors that target the colchicine binding site of tubulin, the vascular targeting modality can be achieved at a lower in vivo concentration than the antiproliferative modality. Thus, agents that target the colchicine binding domain of tubulin can be potentially dual mode agents i.e. antimitotic and antivascular.

There continues to be a need for effective and potent anti-cancer therapy that include efficacy against tumors that are currently untreatable or poorly treatable, efficacy against multi-drug resistant tumors and minimal side effects. The present invention provides compounds, compositions for, and methods of, interfering with microtubular formation and binding tubulin for treating cancer. The compounds of the present invention have great potency in inhibiting tubulin polymerization and at shutting-down tumor vasculature

BACKGROUND PRIOR ART

WO03/101985, published on Dec. 11, 2003, discloses 2-oxo-1,3,4-trihydroquinazolinyl derivatives for the treatment of cell proliferation-related disorders.

EP 1689715, published on Jun. 16, 2005, discloses tubulin inhibitors.

EP 1709011, published on Jun. 16, 2005, discloses 6-phenylalkyl substituted 2-quinolinones and 2-quinoxalinones as poly(ADP-ribose) polymerase inhibitors.

WO2005/117876, published on Dec. 15, 2005, discloses dual small molecule inhibitors of cancer and angiogenesis.

WO 2006/089177, published on Aug. 8, 2006, discloses the use of isozazole combrestatin derivatives for inhibiting tubulin polymerization.

WO2006/118231, published on Nov. 9, 2006 discloses the preparation of 6-(3-pyrazolylamino)pyridines-3-carbonitriles as anti-cancer agents.

WO 2006/003148, published on Jan. 12, 2006, discloses quinazolinedione derivatives as poly(ADP-ribose) polymerase inhibitors.

WO 2007/087684, published on Aug. 6, 2007, discloses substituted benzofurans, benzthiophenes, benzoselenophenes and indoles and their use as tubulin polymerization inhibitors.

WO2008/107478, published on Sep. 12, 2008, discloses quinolinone derivatives as PARP and TANK inhibitors.

Tentori et al., European Journal of Cancer, vol. 43, no. 14, 2007, relates to poly(ADP-ribose)polymerase (PARP) inhibition or PARP-1 gene deletion which reduces angiogenesis.

DESCRIPTION OF THE INVENTION

This invention concerns compounds of formula (I)

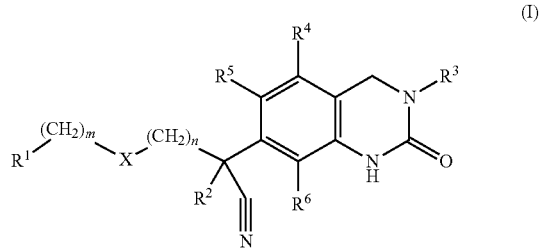

including the stereochemically isomeric forms thereof;
wherein
m is 0, 1 or 2 and when m is 0 then a direct bond is intended;
n is 0, 1 or 2 and when n is 0 then a direct bond is intended;
X is a direct bond, $CR^{10}R^{11}$, $NR^8$ or O;
$R^1$ is aryl or Het;
  wherein aryl is phenyl or naphthalenyl;
  wherein Het is thienyl, pyrrolyl, pyrrolinyl, oxazolyl, thiazolyl, imidazolyl, pyrazolyl, isoxazolyl, isothiazolyl, oxadiazolyl, triazolyl, tetrazolyl, thiadiazolyl, furanyl, piperidinyl, pyridinyl, pyridazinyl, pyrimidinyl, piperazinyl, pyrazinyl, triazinyl, indolizinyl, azaindolizinyl, indolyl, indolinyl, benzothienyl, indazolyl, benzoxazolyl, benzimidazolyl, benzofuranyl, benzothiazolyl, benzotriazolyl, chromanyl, purinyl, quinolinyl, cinnolinyl, phthalazinyl, quinazolinyl, quinoxazolinyl, naphthyridinyl or pteridinyl;
two carbon atoms on aryl or Het can be bridged (i.e. forming a bi- or tricyclic moiety) with a bivalent radical selected from $$—O—CH_2—CH_2—O— \quad (a\text{-}1),$$

$$—CH_2—O—CH_2—O— \quad (a\text{-}2),$$

$$—O—CH_2—CH_2—CH_2— \quad (a\text{-}3),$$

$$—O—CH_2—CH_2—NR^8— \quad (a\text{-}4),$$

$$—O—CR^8{}_2—O— \quad (a\text{-}5),$$

$$—O—CH_2—CH_2— \quad (a\text{-}6),$$

$$—CH_2—N—CH_2—CH_2— \quad (a\text{-}7),$$

$$—(CH_2)_3— \quad (a\text{-}8), \text{ or}$$

$$—(CH_2)_4— \quad (a\text{-}9);$$

each aryl, Het, bridged aryl or bridged Het can be substituted with one, two, three, four or five substituents each independently selected from halo, cyano, nitro, hydroxycarbonyl, $C_{1-6}$alkyl, $C_{2-6}$alkenyl, $C_{2-6}$alkynyl, $C_{3-6}$cycloalkyl, amino$C_{3-6}$cycloalkyl, halo$C_{1-6}$alkyl, trihalo$C_{1-6}$alkyl, $C_{1-6}$alkylcarbonyl, $C_{1-6}$alkyloxycarbonyl, $C_{2-6}$alkenylcarbonyl, oxime, $C_{1-6}$alkyloxime, amidoxime, —C≡C—$CH_2O$—$CH_3$, —C≡C—$CH_2N(CH_3)_2$, —C≡C—Si$(CH_3)_3$, hydroxy$C_{1-6}$alkyl, hydroxy$C_{2-6}$alkenyl, hydroxy$C_{2-6}$alkynyl, cyano$C_{1-6}$alkyl, cyano$C_{2-6}$alkenyl, aminocarbonyl$C_{1-6}$alkyl, $C_{1-6}$alkylsulfonyl$C_{1-6}$alkyl, $C_{1-6}$alkylsulfonyl$C_{2-6}$alkenyl, $C_{1-6}$alkylsulfonyl$C_{2-6}$alkynyl, —PO(O$C_{1-6}$alkyl)$_2$, —B(OH)$_2$, —S—$CH_3$, $SF_5$, $C_{1-6}$alkylsulfonyl, —$NR^8R^9$, —$C_{1-6}$alkyl$NR^8R^9$, —$OR^8$, —$C_{1-6}$alkyl$OR^8$, —$CONR^8R^9$, piperidinyl$C_{1-6}$alkyl, piperazinyl$C_{1-6}$alkyl, $C_{1-6}$alkylpiperazinyl$C_{1-6}$alkyl, morpholinyl$C_{1-6}$alkyl, piperidinyl, piperazinyl, $C_{1-6}$alkylpiperazinyl, morpholinyl, phenyl, thienyl, pyrazolyl, pyrrolyl, pyrrolidinyl, pyridinyl, pyrimidinyl, oxadiazolyl, imidazolyl, imidazolyl$C_{2-6}$alkynyl, $C_{1-6}$alkylimidazolyl$C_{2-6}$alkynyl, cyanopyridinyl, phenyl$C_{1-6}$alkyl, phenyl$C_{2-6}$alkenyl, $C_{1-6}$alkyloxyphenyl, trihalo$C_{1-6}$alkylphenyl, methylpyrazolyl, halopyrimidinyl or dimethylaminopyrrolidinyl;

$R^2$ is hydrogen, methyl, ethyl, propyl, $C_{3-6}$cycloalkyl, $C_{3-6}$cycloalkylmethyl, fluor, phenyl, cyanophenyl or trifluoromethyl;

$R^3$ is methyl, ethyl, propyl, hydroxymethyl, hydroxyethyl, halo, trifluoromethyl, methyloxy or $C_{1-6}$alkylcarbonyl;

each $R^4$, $R^5$ and $R^6$ is independently selected from hydrogen, halo, $C_{1-6}$alkyloxy, cyano, $C_{1-6}$alkyl, —$OCH_2CH_2NR^8R^9$, —$CH_2OCH_2CH_2NR^8R^9$, —$OCH_2CH_2CH_2NR^8R^9$ or $C_{1-6}$alkyloxy$C_{1-6}$alkyloxy;

each $R^8$ and $R^9$ is independently selected from hydrogen, halo, $C_{1-6}$alkyl, $C_{2-6}$alkenyl, $C_{2-6}$alkynyl, carbonyl, $C_{1-6}$alkylsulfonyl$C_{1-6}$alkyl, $C_{1-6}$alkyloxy$C_{1-6}$alkyl, hydroxy$C_{1-6}$alkyl, dihydroxy$C_{1-6}$alkyl, cyano$C_{1-6}$alkyl, trihalo$C_{1-6}$alkyl, phenyl$C_{1-6}$alkyl, (di$C_{1-6}$alkyl)amino$C_{1-6}$alkyl, $C_{1-6}$alkylsulfonyl, morpholinyl$C_{1-6}$alkyl, morpholinylcarbonyl, piperazinyl$C_{1-6}$alkyl, $C_{1-6}$alkylpiperazinyl$C_{1-6}$alkyl, piperidinyl$C_{1-6}$alkyl, thiomorpholinyl$C_{1-6}$alkyl, $C_{3-6}$cycloalkylmethyl, pyridinyl, pyrimidinyl, phenyl, halophenyl, oxanyl$C_{1-6}$alkyl, $C_{1-6}$alkylsulfonyl$C_{1-6}$alkyl or $C_{1-6}$alkylcarbonylamino$C_{1-6}$alkyl;

each $R^{10}$ and $R^{11}$ is independently selected from hydrogen, methyl, hydroxyl; or $R^{10}$ and $R^{11}$ are taken together with the carbon atom to which they are attached to form a cyclopropyl ring or a radical of formula C(=O);

the N-oxide forms thereof, the pharmaceutically acceptable addition salts thereof and the solvates thereof.

The compounds of formula (I) and the intermediates of the invention may also exist in their tautomeric forms. Such forms although not explicitly indicated in the above formula are intended to be included within the scope of the present invention. The tautomeric forms of the compounds of formula (I) are meant to comprise those compounds of formula (I) wherein e.g. an enol group is converted into a keto group (keto-enol tautomerism).

Whenever the heterocyclic ring systems in $R^1$ contain a —$CH_2$—, —CH=, or —NH— moiety the substituents or the rest of the molecule can be attached to each carbon or nitrogen atom implying that one or both hydrogen atoms on the same carbon atom may be replaced.

A number of terms used in the foregoing definitions and hereinafter are explained hereunder. These terms are sometimes used as such or in composite terms.

As used in the foregoing definitions and hereinafter, halo is generic to fluoro, chloro, bromo and iodo; $C_{1-6}$alkyl defines straight and branched chain saturated hydrocarbon radicals having from 1 to 6 carbon atoms such as, e.g. methyl, ethyl, propyl, butyl, pentyl, hexyl, 1-methylethyl, 2-methylpropyl, 2-methyl-butyl, 2-methylpentyl and the like; halo$C_{1-6}$alkyl defines $C_{1-6}$alkyl containing one halo substituent, for example fluoromethyl (—$CH_2F$); trihalo$C_{1-6}$alkyl defines $C_{1-6}$alkyl containing three identical or different halo substituents for example trifluoromethyl; $C_{2-6}$alkenyl defines straight and branched chain hydrocarbon radicals containing a double bond, in particular one double bond, and having from 2 to 6 carbon atoms such as, for example, ethenyl, 2-propenyl, 3-butenyl, 2-pentenyl, 3-pentenyl, 3-methyl-2-butenyl, and the like; $C_{2-6}$alkynyl defines straight and branched chain hydrocarbon radicals containing a triple bond, in particular one triple bond, and having from 2 to 6 carbon atoms, such as, for example, ethynyl, 2-propynyl, 3-butynyl, 2-butynyl, 2-pentynyl, 3-pentynyl, 3-hexynyl, and the like; $C_{3-6}$cycloalkyl includes cyclic hydrocarbon groups having from 3 to 6 carbons, such as cyclopropyl, cyclobutyl, cyclopentyl, cyclohexyl and the like.

The term "pharmaceutically acceptable addition salts" means pharmaceutically acceptable acid or base addition salts. The pharmaceutically acceptable acid or base addition salts as mentioned hereinabove or hereinafter are meant to comprise the therapeutically active non-toxic acid and non-toxic base addition salt forms which the compounds of formula (I) are able to form. The compounds of formula (I)

which have basic properties can be converted in their pharmaceutically acceptable acid addition salts by treating said base form with an appropriate acid. Appropriate acids comprise, for example, inorganic acids such as hydrohalic acids, e.g. hydrochloric or hydrobromic acid; sulfuric; nitric; phosphoric and the like acids; or organic acids such as, for example, acetic, propanoic, hydroxyacetic, lactic, pyruvic, oxalic, malonic, succinic (i.e. butanedioic acid), maleic, fumaric, malic, tartaric, citric, methanesulfonic, ethanesulfonic, benzenesulfonic, p-toluenesulfonic, cyclamic, salicylic, p-aminosalicylic, pamoic and the like acids.

The compounds of formula (I) which have acidic properties may be converted in their pharmaceutically acceptable base addition salts by treating said acid form with a suitable organic or inorganic base. Appropriate base salt forms comprise, for example, the ammonium salts, the alkali and earth alkaline metal salts, e.g. the lithium, sodium, potassium, magnesium, calcium salts and the like, salts with organic bases, e.g. the benzathine, N-methyl-D-glucamine, hydrabamine salts, and salts with amino acids such as, for example, arginine, lysine and the like.

For therapeutic use, salts of the compounds of formula (I) are those wherein the counterion is pharmaceutically acceptable. However, salts of acids and bases which are non-pharmaceutically acceptable may also find use, for example, in the preparation or purification of a pharmaceutically acceptable compound. All salts, whether pharmaceutically acceptable or not are included within the ambit of the present invention.

A quaternary ammonium salt of a compound according to formula (I) defines said compound which is able to form by a reaction between a basic nitrogen of a compound according to formula (I) and an appropriate quaternizing agent, such as, for example, an optionally substituted alkylhalide, arylhalide or arylalkylhalide, in particular methyliodide and benzyliodide. Other reactants with good leaving groups may also be used, such as, for example, alkyl trifluoromethanesulfonates, alkyl methanesulfonates and alkyl p-toluenesulfonates. A quaternary ammonium salt has at least one positively charged nitrogen. Pharmaceutically acceptable counterions include chloro, bromo, iodo, trifluoroacetate and acetate ions. The quaternary ammonium salts of the compounds of formula (I) are included within the ambit of the present invention.

The terms solvates comprise the hydrates and the solvent addition forms which the compounds of formula (I) are able to form and the pharmaceutically acceptable addition salts thereof. Examples of such forms are e.g. hydrates, alcoholates and the like.

The term stereochemically isomeric forms of compounds of formula (I), as used hereinbefore or hereinafter, defines all possible compounds made up of the same atoms bonded by the same sequence of bonds but having different three-dimensional structures which are not interchangeable, which the compounds of formula (I) may possess. Unless otherwise mentioned or indicated, the chemical designation of a compound encompasses the mixture of all possible stereochemically isomeric forms which said compound may possess. Said mixture may contain all diastereomers and/or enantiomers of the basic molecular structure of said compound. All stereochemically isomeric forms of the compounds of formula (I) both in pure form or in admixture with each other are intended to be embraced within the scope of the present invention.

Of special interest are those compounds of formula (I) which are stereochemically pure. Pure stereoisomeric forms of the compounds and intermediates as mentioned herein are defined as isomers substantially free of other enantiomeric or diastereomeric forms of the same basic molecular structure of said compounds or intermediates. In particular, the term "stereoisomerically pure" concerns compounds or intermediates having a stereoisomeric excess of at least 80% (i.e. minimum 80% of one isomer and maximum 20% of the other possible isomers) up to a stereoisomeric excess of 100% (i.e. 100% of one isomer and none of the other), more in particular, compounds or intermediates having a stereoisomeric excess of 90% up to 100%, even more in particular having a stereoisomeric excess of 94% up to 100% and most in particular having a stereoisomeric excess of 97% up to 100%. The terms "enantiomerically pure" and "diastereomerically pure" should be understood in a similar way, but then having regard to the enantiomeric excess, respectively the diastereomeric excess of the mixture in question.

If a compound is bearing one chiral centre and the two enantiomers of this compound have been separated, an asterix "*" in the drawing indicates that the absolute stereochemistry of the enantiomer has not been determined.

The N-oxide forms of the compounds of formula (I) are meant to comprise those compounds of formula (I) wherein one or several tertiary nitrogen atoms are oxidized to the so-called N-oxide, particularly those N-oxides wherein one or more of the piperidine- or piperazine nitrogens are N-oxidized.

The compounds of formula (I) may be converted to the corresponding N-oxide forms following art-known procedures for converting a trivalent nitrogen into its N-oxide form. Said N-oxidation reaction may generally be carried out by reacting the starting material of formula (I) with an appropriate organic or inorganic peroxide. Appropriate inorganic peroxides comprise, for example, hydrogen peroxide, alkali metal or earth alkaline metal peroxides, e.g. sodium peroxide, potassium peroxide; appropriate organic peroxides may comprise peroxy acids such as, for example, benzenecarboperoxoic acid or halo substituted benzenecarboperoxoic acid, e.g. 3-chlorobenzenecarboperoxoic acid, peroxoalkanoic acids, e.g. peroxoacetic acid, alkylhydroperoxides, e.g. t-butyl hydro-peroxide. Suitable solvents are, for example, water, lower alcohols, e.g. ethanol and the like, hydrocarbons, e.g. toluene, ketones, e.g. 2-butanone, halogenated hydrocarbons, e.g. dichloromethane, and mixtures of such solvents.

The present invention is also intended to include any isotopes of atoms present in the compounds of the invention. For example, isotopes of hydrogen include tritium and deuterium and isotopes of carbon include C-13 and C-14.

Whenever used hereinafter, the term "compounds of formula (I)" is meant to include also the N-oxide forms, the pharmaceutically acceptable acid or base addition salts, the solvates and all stereoisomeric forms thereof.

A first group of interesting compounds are those compounds of formula (I) wherein
m is 0, 1 or 2 and when m is 0 then a direct bond is intended;
n is 0, 1 or 2 and when n is 0 then a direct bond is intended;
X is a direct bond, $CR^{10}R^{11}$, $NR^8$ or O;
$R^1$ is aryl or Het;
  wherein aryl is phenyl or naphthalenyl;
  wherein Het is thienyl, pyrrolyl, pyrrolinyl, oxazolyl, thiazolyl, imidazolyl, pyrazolyl, isoxazolyl, isothiazolyl, oxadiazolyl, triazolyl, tetrazolyl, thiadiazolyl, furanyl, piperidinyl, pyridinyl, pyridazinyl, pyrimidinyl, piperazinyl, pyrazinyl, triazinyl, indolizinyl, azaindolizinyl, indolyl, indolinyl, benzothienyl, indazolyl, benzoxazolyl, benzimidazolyl, benzofuranyl, benzothiazolyl, benzotriazolyl, chromanyl, purinyl, quinolinyl, cinnolinyl, phthalazinyl, quinazolinyl, quinoxalinyl, naphthyridinyl or pteridinyl;

two carbon atoms on aryl or Het can be bridged (i.e. forming a bi- or tricyclic moiety) with a bivalent radical selected from $$-O-CH_2-CH_2-O- \quad (a\text{-}1),$$

$$-CH_2-O-CH_2-O- \quad (a\text{-}2),$$

$$-O-CH_2-CH_2-CH_2- \quad (a\text{-}3),$$

$$-O-CH_2-CH_2-NR^8- \quad (a\text{-}4),$$

$$-O-CR^8{}_2-O- \quad (a\text{-}5),$$

$$-O-CH_2-CH_2- \quad (a\text{-}6),$$

$$-CH_2-N-CH_2-CH_2- \quad (a\text{-}7),$$

$$-(CH_2)_3- \quad (a\text{-}8), \text{ or}$$

$$-(CH_2)_4- \quad (a\text{-}9);$$

each aryl, Het, bridged aryl or bridged Het can be substituted with one, two, three, four or five substituents each independently selected from halo, cyano, nitro, hydroxycarbonyl, $C_{1-6}$alkyl, $C_{2-6}$alkenyl, $C_{2-6}$alkynyl, $C_{3-6}$cycloalkyl, amino$C_{3-6}$cycloalkyl, halo$C_{1-6}$alkyl, trihalo$C_{1-6}$alkyl, $C_{1-6}$alkylcarbonyl, $C_{1-6}$alkyloxycarbonyl, $C_{2-6}$alkenylcarbonyl, oxime, $C_{1-6}$alkyloxime, amidoxime, $-C\equiv C-CH_2O-CH_3$, $-C\equiv C-CH_2N(CH_3)_2$, $-C\equiv C-Si(CH_3)_3$, hydroxy$C_{1-6}$alkyl, hydroxy$C_{2-6}$alkenyl, hydroxy$C_{2-6}$alkynyl, cyano$C_{1-6}$alkyl, cyano$C_{2-6}$alkenyl, aminocarbonyl$C_{1-6}$alkyl, $C_{1-6}$alkylsulfonyl$C_{1-6}$alkyl, $C_{1-6}$alkylsulfonyl$C_{2-6}$alkenyl, $C_{1-6}$alkylsulfonyl$C_{2-6}$alkynyl, $-PO(OC_{1-6}alkyl)_2$, $-B(OH)_2$, $-S-CH_3$, $SF_5$, $C_{1-6}$alkylsulfonyl, $-NR^8R^9$, $C_{1-6}$alkyl$NR^8R^9$, $-OR^8$, $-C_{1-6}$alkyl$OR^8$, $-CONR^8R^9$, piperidinyl$C_{1-6}$alkyl, piperazinyl$C_{1-6}$alkyl, $C_{1-6}$alkylpiperazinyl$C_{1-6}$alkyl, morpholinyl$C_{1-6}$alkyl, piperidinyl, piperazinyl, $C_{1-6}$alkylpiperazinyl, morpholinyl, phenyl, thienyl, pyrazolyl, pyrrolyl, pyrrolidinyl, pyridinyl, pyrimidinyl, oxadiazolyl, imidazolyl, imidazolyl$C_{2-6}$alkynyl, $C_{1-6}$alkylimidazolyl$C_{2-6}$alkynyl, cyanopyridinyl, phenyl$C_{1-6}$alkyl, phenyl$C_{2-6}$alkenyl, morpholinyl$C_{1-6}$alkyl, $C_{1-6}$alkyloxyphenyl, trihalo$C_{1-6}$alkylphenyl, methylpyrazolyl, halopyrimidinyl or dimethylaminopyrrolidinyl;

$R^2$ is hydrogen, methyl, ethyl, propyl, $C_{3-6}$cycloalkyl, $C_{3-6}$cycloalkylmethyl, fluor, phenyl, cyanophenyl or trifluoromethyl;

$R^3$ is methyl, ethyl, propyl, hydroxymethyl, halo, trifluoromethyl, methyloxy or $C_{1-6}$alkylcarbonyl;

each $R^4$, $R^5$ and $R^6$ is independently selected from hydrogen, halo, $C_{1-6}$alkyloxy, cyano, $C_{1-6}$alkyl, $-OCH_2CH_2NR^8R^9$, $-CH_2OCH_2CH_2NR^8R^9$, $-OCH_2CH_2CH_2NR^8R^9$ or $C_{1-6}$alkyloxy$C_{1-6}$alkyloxy;

each $R^8$ and $R^9$ is independently selected from hydrogen, halo, $C_{1-6}$alkyl, $C_{2-6}$alkenyl, $C_{2-6}$alkynyl, carbonyl, $C_{1-6}$alkylsulfonyl$C_{1-6}$alkyl, $C_{1-6}$alkyloxy$C_{1-6}$alkyl, hydroxy$C_{1-6}$alkyl, dihydroxy$C_{1-6}$alkyl, cyano$C_{1-6}$alkyl, trihalo$C_{1-6}$alkyl, phenyl$C_{1-6}$alkyl, $(diC_{1-6}alkyl)amino$C_{1-6}$alkyl, $C_{1-6}$alkylsulfonyl, morpholinyl$C_{1-6}$alkyl, morpholinylcarbonyl, piperazinyl$C_{1-6}$alkyl, $C_{1-6}$alkylpiperazinyl$C_{1-6}$alkyl, piperidinyl$C_{1-6}$alkyl, thiomorpholinyl$C_{1-6}$alkyl, $C_{3-6}$cycloalkylmethyl, pyrimidinyl, phenyl, halophenyl, oxanyl$C_{1-6}$alkyl, $C_{1-6}$alkylsulfonyl$C_{1-6}$alkyl or $C_{1-6}$alkylcarbonylamino$C_{1-6}$alkyl;

each $R^{10}$ and $R^{11}$ is independently selected from hydrogen, methyl, hydroxyl, or taken together with the carbon atom to which they are attached can form a cyclopropyl ring or a radical of formula $C(=O)$;

the N-oxide forms, the pharmaceutically acceptable addition salts, the solvates and the stereo-chemically isomeric forms thereof.

A second group of interesting compounds consists of those compounds of formula (I) wherein one or more of the following restrictions apply:
a) m is 0 or 1;
b) $R^1$ is phenyl or Het; wherein Het is pyridinyl, pyrimidinyl or benzothiazolyl;
c) two carbon atoms on Het are bridged with the bivalent radical (a-8);
d) each phenyl or Het or bridged Het in the definition of $R^1$ can be substituted with one or two substituents each independently selected from halo, cyano, $C_{1-6}$alkyl, $C_{2-6}$ alkynyl, $-C\equiv C-CH_2O-CH_3$, hydroxy$C_{2-6}$ alkynyl or $-OR^8$;
e) $R^2$ is methyl or ethyl;
f) $R^3$ is methyl, ethyl or hydroxyethyl;
g) each $R^4$, $R^5$ and $R^6$ is independently selected from hydrogen or halo;
h) each $R^8$ is hydrogen or $C_{1-6}$alkyl; or
i) each $R^{10}$ and $R^{11}$ is hydrogen.

A third group of interesting compounds consists of those compounds of formula (I) or the above group of interesting compounds of formula (I) wherein Het is pyridinyl or pyrimidinyl.

A fourth group of interesting compounds consists of those compounds of formula (I) or of one of the above groups of interesting compounds of formula (I) wherein one or more of the following restrictions apply:
a) m is 0 and n is 0;
b) X is a direct bond or $CH_2$;
c) $R^1$ is phenyl, pyridinyl or pyrimidinyl;
d) when $R^1$ is pyridinyl two carbon atoms on the pyridinyl can be bridged with the bivalent radical (a-8);
e) each phenyl, pyridinyl or pyrimidinyl in the definition of $R^1$ can be substituted with one or two substituents each independently selected from halo, cyano or $C_{1-6}$alkyloxy;
f) $R^2$ is methyl;
g) $R^3$ is methyl or ethyl; or
h) each $R^4$, $R^5$ and $R^6$ is hydrogen.

A fifth group of interesting compounds consists of those compounds of formula (I) or of one of the above groups of interesting compounds of formula (I) wherein one or more of the following restrictions apply:
a) X is a direct bond and two carbon atoms on aryl or Het are bridged with a bivalent radical selected from (a-8);
b) X is $CR^{10}R^{11}$ and m and n are 0;
d) X is $NR^8$ and m is 1 and n is 1;
e) X is O and m is 0 and n is 2;
g) $R^2$ is methyl; or
h) $R^3$ is ethyl.

A sixth group of interesting compounds consists of those compounds of formula (I) or of one of the above groups of interesting compounds of formula (I) wherein $R^3$ is hydroxyethyl.

A group of preferred compounds consists of those compounds of formula (I) wherein m is 0 or 1; $R^1$ is phenyl or Het; wherein Het is pyridinyl, pyrimidinyl or benzothiazolyl; two carbon atoms on Het can be bridged with the bivalent radical (a-8); each phenyl or Het or bridged Het can be substituted with one or two substituents each independently selected from halo, cyano, $C_{1-6}$alkyl, $C_{2-6}$alkynyl, $-C\equiv C-CH_2-CH_3$, hydroxy$C_{2-6}$alkynyl or $-OR^8$; $R^2$ is methyl or ethyl; $R^3$ is methyl, ethyl or hydroxyethyl; each $R^4$, $R^5$ and $R^6$ is independently selected from hydrogen or halo; each $R^8$ is hydrogen or $C_{1-6}$alkyl; and each $R^{10}$ and $R^{11}$ is hydrogen.

A group of more preferred compounds consists of those compounds of formula (I) wherein m is 0 and n is 0; X is a direct bond or $CH_2$; $R^1$ is phenyl, pyridinyl or pyrimidinyl; when $R^1$ is pyridinyl two carbon atoms on the pyridinyl can be bridged with the bivalent radical (a-8); each phenyl, pyridinyl or pyrimidinyl can be substituted with one or two substituents each independently selected from halo, cyano or $C_{1-6}$alkyloxy; $R^2$ is methyl; $R^3$ is methyl or ethyl; and each $R^4$, $R^5$ and $R^6$ is hydrogen.

The most preferred compounds are Co. No. 1, Co. No. 6, Co. No. 27, Co. No. 13 and Co. No. 4.

Co. No. 1

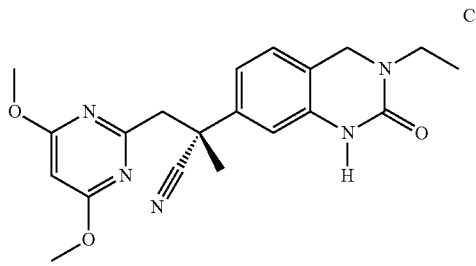

Co. No. 6

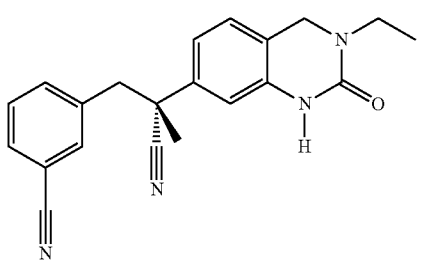

Co. No. 27

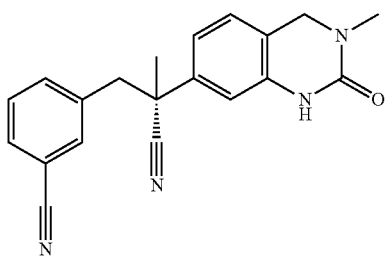

Co. No. 13

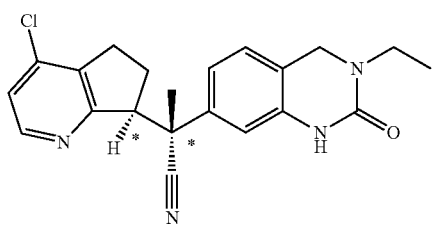

Co. No. 4

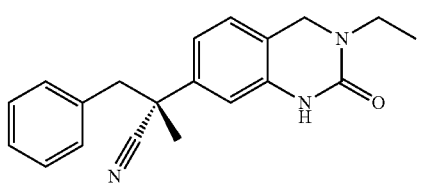

* relative configurations and the N-oxide forms thereof, the pharmaceutically acceptable addition salts thereof and the solvates thereof; in particular and the pharmaceutically acceptable addition salts thereof and the solvates thereof; more in particular and the pharmaceutically acceptable addition salts thereof.

The compounds of formula (I) can be prepared according to the general methods described herein below. The starting materials and some of the intermediates are known compounds and are commercially available or may be prepared according to conventional reaction procedures generally known in the art.

Some preparation methods will be described hereinafter in more detail. Other methods for obtaining final compounds of formula (I) are described in the examples.

Compounds of formula (I) can be prepared by adding an excess of a base, for example 2-methyl-2-propanol, potassium salt or lithium diisopropylamide to intermediates of formula (II) in the presence of intermediates of formula (III), wherein W is chloro or bromo or another leaving group such as mesylate, in a suitable solvent such as tetrahydrofuran, dioxane or dimethylformamide.

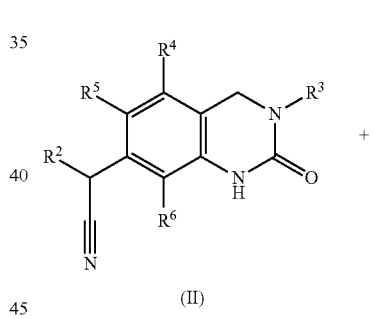

(II)

+

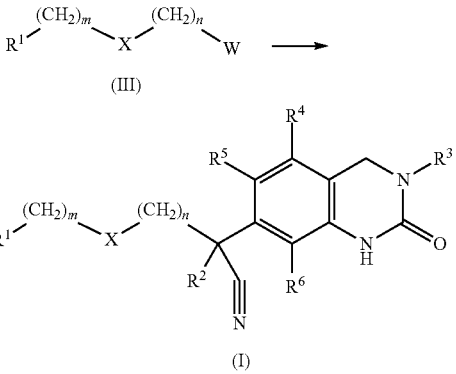

Intermediates of formula (II), wherein $R^3$ is methyl, ethyl or propyl or wherein $R^3$ is —$CH_2$—$CH_2$—O—$Si(CH_3)_2tBu$, can be prepared by adding a mixture of 2-methyl-2-propanol, potassium salt and tosylmethyl isocyanide in dimethylsulfoxide (DMSO) to an intermediate of formula (IV) in a suitable solvent such as methanol.

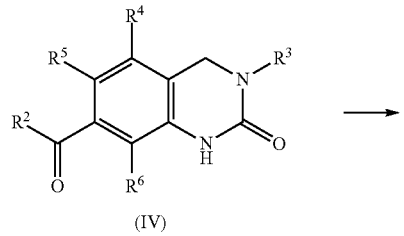

(IV)

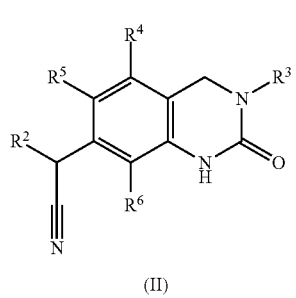

(II)

Intermediates of formula (IV) can be prepared by treating an intermediate of formula (V) with an organolithium reagent such as, e.g. n-butyllithium in a reaction inert solvent, e.g. tetrahydrofuran, and subsequently reacting said intermediate with an intermediate of formula (VI).

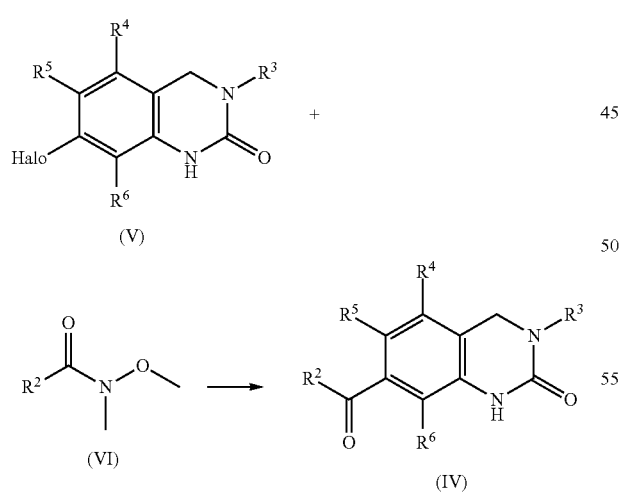

Intermediates of formula (IV) can also be prepared by converting intermediates of formula (VII) in the presence of a suitable oxidant such as manganese dioxide in a suitable solvent such as dioxane or in the presence of potassium manganese tetraoxide in Tris[2-(2-methoxyethoxy)ethyl]amine, in a suitable solvent such as dichloromethane.

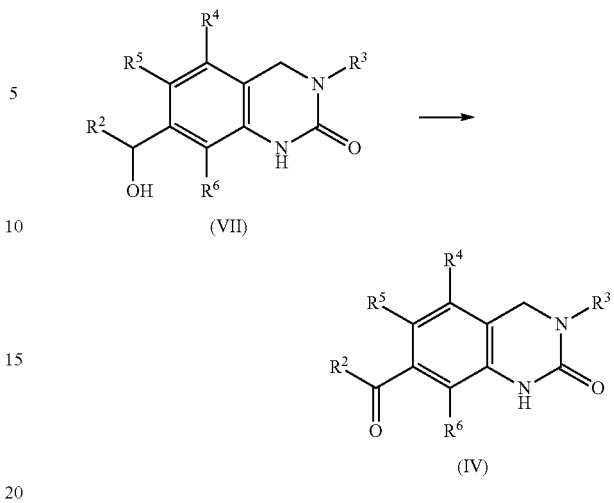

Intermediates of formula (VII) can be prepared by treating an intermediate of formula (VIII) with an organolithium reagent such as, e.g. n-butyllithium in a reaction inert solvent, e.g. tetrahydrofuran, and subsequently reacting said intermediate with an intermediate of formula (V).

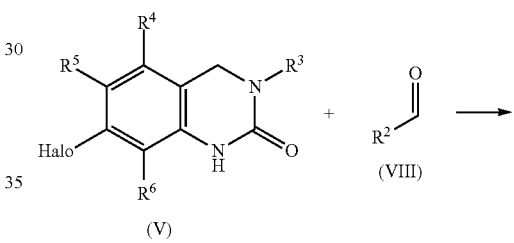

Intermediates of formula (V) can be prepared by reacting carbonyldiimidazole with intermediates of formula (IX) in a suitable solvent such as tetrahydrofuran.

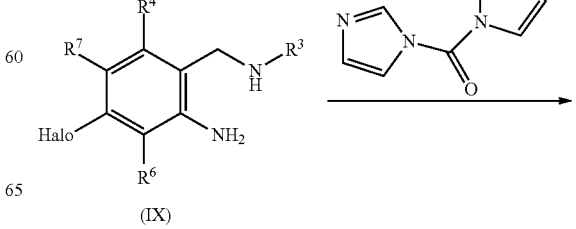

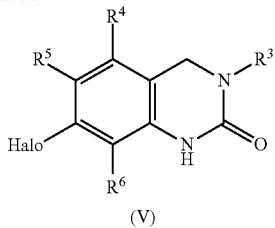

(V)

Intermediates of formula (IX) can be prepared by reduction of the nitro moiety of intermediates of formula (X) by hydrogenation in the presence of a platine catalyst such as $PtO_2$, in a suitable solvent such as methanol. Such reduction can also be performed by other art-known procedure, for example using iron and ammonium chloride in a mixture of solvent such as tetrahydrofuran and water.

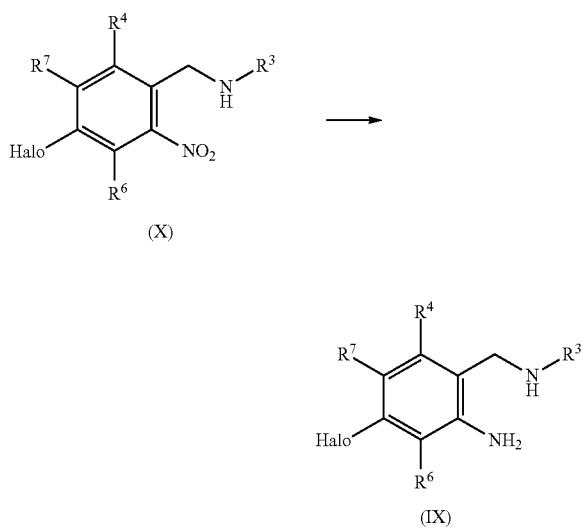

Intermediates of formula (X) can be prepared by reacting a primary amine (XII) with intermediates of formula (XI) in the presence of a base such as potassium carbonate, in a suitable solvent such as acetonitrile. Such reaction can also be performed by other art-known procedures, for example by using methanol at reflux.

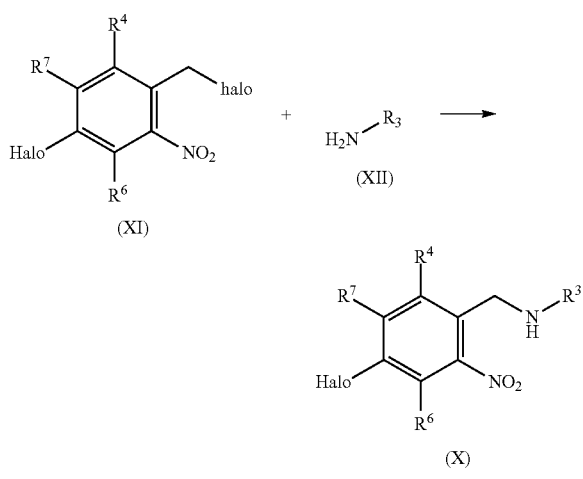

The compounds of formula (I) or their intermediates may also be converted into each other via art-known reactions or functional group transformations. Some of such transformations are already described hereinabove. Other examples are hydrolysis of carboxylic esters to the corresponding carboxylic acid or alcohol; hydrolysis of amides to the corresponding carboxylic acids or amines; hydrolysis of nitriles to the corresponding amides; amino groups on imidazole or phenyl may be replaced by a hydrogen by art-known diazotation reactions and subsequent replacement of the diazo-group by hydrogen; alcohols may be converted into esters and ethers; primary amines may be converted into secondary or tertiary amines; double bonds may be hydrogenated to the corresponding single bond; an iodo radical on a phenyl group may be converted into an ester group by carbon monoxide insertion in the presence of a suitable palladium catalyst; an iodo radical on a phenyl group may be converted into a $C_{2-6}$alkynyl group or a derivative thereof (e.g. —C≡C—Si(CH$_3$)$_3$ or hydroxyC$_{2-6}$alkynyl) by reaction with the suitable $C_{2-6}$alkynyl compound or derivative thereof in the presence of a suitable palladium catalyst; a —C≡C—Si(CH$_3$)$_3$ radical on a phenyl group may be converted into —C≡CH in the presence of a suitable base.

Some of the compounds of formula (I) and some of the intermediates in the present invention may contain an asymmetric carbon atom. Pure stereochemically isomeric forms of said compounds and said intermediates can be obtained by the application of art-known procedures. For example, diastereoisomers can be separated by physical methods such as selective crystallization or chromatographic techniques, e.g. counter current distribution, liquid chromatography and the like methods. Enantiomers can be obtained from racemic mixtures by first converting said racemic mixtures with suitable resolving agents such as, for example, chiral acids, to mixtures of diastereomeric salts or compounds; then physically separating said mixtures of diastereomeric salts or compounds by, for example, selective crystallization, supercritical fluid chromatography or chromatographic techniques, e.g. liquid chromatography and the like methods; and finally converting said separated diastereomeric salts or compounds into the corresponding enantiomers. Pure stereochemically isomeric forms may also be obtained from the pure stereochemically isomeric forms of the appropriate intermediates and starting materials, provided that the intervening reactions occur stereospecifically.

The present invention also relates to a compound of formula (I) as defined above for use as a medicine, in particular for use in the treatment of a tubelin polymerization mediated disorder, for use to inhibit abnormal growth of cells, for use to inhibit tumor growth.

The compounds of the present invention are tubulin polymerization inhibitors as can be seen from the experimental part hereinunder.

The term "tubulin polymerization inhibitor" is used to identify a compound that
- stabilize microtubules, inhibit the depolymerization of microtubules, stabilizes the microtubules or freeze the microtubular structure,
- disrupt polymerization of microtubules and disrupt microtubular formation, or
- destabilize microtubules and prevent microtubule formation.

As the consequence of the tubulin polymerization inhibiting capacity the compounds of the present invention also have vasculature disrupting capacities.

The pharmacokinetic properties (absorption, distribution, metabolism, excretion and toxicity) of the drug are important in attaining the maximum therapeutic index. It has been reported that a low volume of distribution (concentration of the drug in the vasculature) and short half-life are desirable for vasculature disrupting agents. A low volume of distribution maximises drug exposure to the target tissue, vasculature endothelium, and minimises exposure to other tissues (outside the vasculature). Also, tumour vasculature shuts down very quickly upon exposure to a vasculature disrupting agent, so that ongoing exposure systematically is undesirable as it will not further affect the tumour and may lead to side-effects.

The present invention also contemplates the use of compounds in the preparation of a medicament for the treatment of any of the diseases and disorders in an animal, particularly a human, described herein.

The present invention also contemplates the use of compounds of formula (I) for the manufacture of a medicament for the treatment of a tubulin polymerization mediated disorder.

The present invention also comprises a pharmaceutical composition comprising a pharmaceutically acceptable carrier and as an active ingredient a therapeutically effective amount of a compound of the present invention.

To prepare the pharmaceutical compositions of this invention, an effective amount of a particular compound, in base or acid addition salt form, as the active ingredient is combined in intimate admixture with a pharmaceutically acceptable carrier, which carrier may take a wide variety of forms depending on the form of preparation desired for administration. These pharmaceutical compositions are desirably in unitary dosage form suitable, preferably, for administration orally, rectally, percutaneously, or by parenteral injection. For example, in preparing the compositions in oral dosage form, any of the usual pharmaceutical media may be employed, such as, for example, water, glycols, oils, alcohols and the like in the case of oral liquid preparations such as suspensions, syrups, elixirs and solutions; or solid carriers such as starches, sugars, kaolin, lubricants, binders, disintegrating agents and the like in the case of powders, pills, capsules and tablets. Because of their ease in administration, tablets and capsules represent the most advantageous oral dosage unit form, in which case solid pharmaceutical carriers are obviously employed. For parenteral compositions, the carrier will usually comprise sterile water, at least in large part, though other ingredients, to aid solubility for example, may be included. Injectable solutions, for example, may be prepared in which the carrier comprises saline solution, glucose solution or a mixture of saline and glucose solution. Injectable suspensions may also be prepared in which case appropriate liquid carriers, suspending agents and the like may be employed. In the compositions suitable for percutaneous administration, the carrier optionally comprises a penetration enhancing agent and/or a suitable wetting agent, optionally combined with suitable additives of any nature in minor proportions, which additives do not cause a significant deleterious effect to the skin. Said additives may facilitate the administration to the skin and/or may be helpful for preparing the desired compositions. These compositions may be administered in various ways, e.g., as a transdermal patch, as a spot-on, as an ointment. It is especially advantageous to formulate the aforementioned pharmaceutical compositions in dosage unit form for ease of administration and uniformity of dosage. Dosage unit form as used in the specification and claims herein refers to physically discrete units suitable as unitary dosages, each unit containing a predetermined quantity of active ingredient calculated to produce the desired therapeutic effect in association with the required pharmaceutical carrier. Examples of such dosage unit forms are tablets (including scored or coated tablets), capsules, pills, powder packets, wafers, injectable solutions or suspensions, teaspoonfuls, tablespoonfuls and the like, and segregated multiples thereof.

The term "treatment" as used herein covers any treatment of a disease and/or condition in an animal, particularly a human, and includes: (i) preventing a disease and/or condition from occurring in a subject which may be predisposed to the disease and/or condition but has not yet been diagnosed as having it; (ii) inhibiting the disease and/or condition, i.e., arresting its development; (iii) relieving the disease and/or condition, i.e., causing regression of the disease and/or condition. Preferably, the term "treatment" means (ii) or (iii).

This invention provides a method for inhibiting the abnormal growth of cells, including transformed cells, by administering an effective amount of a compound of the present invention to a subject, e.g. a mammal (and more particularly a human) in need of such treatment. Abnormal growth of cells refers to cell growth independent of normal regulatory mechanisms (e.g. loss of contact inhibition). This includes the inhibition of tumour growth both directly by causing growth arrest, terminal differentiation and/or apoptosis of cancer cells, and indirectly, by inhibiting neovascularization of tumours.

The compounds, compositions and methods of the present invention are particularly useful for treating or preventing tissue damage resulting from cell death or damage due to necrosis or apoptosis.

The compounds of the present invention can be "anti-cancer agents", which term also encompasses "anti-tumor cell growth agents" and "anti-neoplastic agents".

This invention also provides a method for inhibiting tumour growth by administering an effective amount of a compound of the present invention, to a subject, e.g. a mammal (and more particularly a human) in need of such treatment.

This invention also provides the use of a compound of formula (I) for the manufacture of a medicament for the inhibition of tumor growth.

Examples of tumours, including adult and pediatric malignancies, which may be inhibited by the compounds of the present invention include, but are not limited to, lung cancer including small cell lung cancer and non-small cell lung cancer (e.g. adenocarcinoma), pancreatic cancers (e.g. pancreatic carcinoma such as, for example exocrine pancreatic carcinoma), colon cancers (e.g. colorectal carcinomas, such as, for example, colon adenocarcinoma and colon adenoma), oesophageal cancer, oral squamous carcinoma, tongue carcinoma, gastric carcinoma, liver cancer, nasopharyngeal cancer, hematopoietic tumours of lymphoid lineage (e.g. acute lymphocytic leukemia, B-cell lymphoma, Burkitt's lymphoma), non-Hodgkin's lymphoma (e.g. mantle cell lymphoma), Hodgkin's disease, myeloid leukemias (for example, acute myelogenous leukemia (AML) or chronic myelogenous leukemia (CML)), acute lymphoblastic leukemia, chronic lymphocytic leukemia (CLL), thyroid follicular cancer, myelodysplastic syndrome (MDS), tumours of mesenchymal origin, soft tissue sarcomas, liposarcomas, gastrointestinal stromal sarcomas, malignant peripheral nerve sheath tumours (MPNST), Ewing sarcomas, leiomyosarcomas, mesenchymal chondrosarcomas, lymphosarcomas, fibrosarcomas, rhabdomyosarcomas, melanomas, teratocarcinomas, neuroblastomas, brain tumours, medulloblastoma, gliomas, benign tumour of the skin (e.g. keratoacanthomas), breast carcinoma (e.g. advanced breast cancer), kidney carcinoma, nephroblastoma, ovary carcinoma, cervical carcinoma, endometrial carcinoma, bladder carcinoma, prostate cancer including the advanced disease and hormone refractory prostate cancer, testicular cancers, osteosarcoma, head and neck cancer, epidermal carcinoma, multiple myeloma (e.g. refractory multiple myeloma), mesothelioma. Particular cancers that can be treated with the compounds of the present invention are breast cancer, colorectal cancer, non-small cell lung cancer, acute myelogenous leukemia (AML).

As another aspect of the present invention, a combination of a compound with tubulin binding properties of formula (I) with another anticancer agent is envisaged, especially for use as a medicine, more specifically in the treatment of cancer or related diseases. For the treatment of the above conditions, the compounds of the invention may be advantageously employed in combination with one or more other medicinal agents, more particularly, with other anti-cancer agents or adjuvants in cancer therapy. Examples of anti-cancer agents or adjuvants (supporting agents in the therapy) include but are not limited to:

- platinum coordination compounds for example cisplatin optionally combined with amifostine, carboplatin or oxaliplatin;
- taxane compounds for example paclitaxel, paclitaxel protein bound particles (Abraxane™) or docetaxel;
- topoisomerase I inhibitors such as camptothecin compounds for example irinotecan, SN-38, topotecan, topotecan hcl;
- topoisomerase II inhibitors such as anti-tumour epipodophyllotoxins or podophyllotoxin derivatives for example etoposide, etoposide phosphate or teniposide;
- anti-tumour vinca alkaloids for example vinblastine, vincristine or vinorelbine;
- anti-tumour nucleoside derivatives for example 5-fluorouracil, leucovorin, gemcitabine, gemcitabine hcl, capecitabine, cladribine, fludarabine, nelarabine;
- alkylating agents such as nitrogen mustard or nitrosourea for example cyclophosphamide, chlorambucil, carmustine, thiotepa, mephalan (melphalan), lomustine, altretamine, busulfan, dacarbazine, estramustine, ifosfamide optionally in combination with mesna, pipobroman, procarbazine, streptozocin, telozolomide, uracil;
- anti-tumour anthracycline derivatives for example daunorubicin, doxorubicin optionally in combination with dexrazoxane, doxil, idarubicin, mitoxantrone, epirubicin, epirubicin hcl, valrubicin;
- molecules that target the IGF-1 receptor for example picropodophilin;
- tetracarcin derivatives for example tetrocarcin A;
- glucocorticoïden for example prednisone;
- antibodies for example trastuzumab (HER2 antibody), rituximab (CD20 antibody), gemtuzumab, gemtuzumab ozogamicin, cetuximab, pertuzumab, bevacizumab, alemtuzumab, eculizumab, ibritumomab tiuxetan, nofetumomab, panitumumab, tositumomab, CNTO 328;
- estrogen receptor antagonists or selective estrogen receptor modulators or inhibitors of estrogen synthesis for example tamoxifen, fulvestrant, toremifene, droloxifene, faslodex, raloxifene or letrozole;
- aromatase inhibitors such as exemestane, anastrozole, letrazole, testolactone and vorozole;
- differentiating agents such as retinoids, vitamin D or retinoic acid and retinoic acid metabolism blocking agents (RAMBA) for example accutane;
- DNA methyl transferase inhibitors for example azacytidine or decitabine;
- antifolates for example premetrexed disodium;
- antibiotics for example antinomycin D, bleomycin, mitomycin C, dactinomycin, caminomycin, daunomycin, levamisole, plicamycin, mithramycin;
- antimetabolites for example clofarabine, aminopterin, cytosine arabinoside or methotrexate, azacitidine, cytarabine, floxuridine, pentostatin, thioguanine;
- apoptosis inducing agents and antiangiogenic agents such as Bcl-2 inhibitors for example YC 137, BH 312, ABT 737, gossypol, HA 14-1, TW 37 or decanoic acid;
- tubuline-binding agents for example combrestatin, colchicines or nocodazole;
- kinase inhibitors (e.g. EGFR (epithelial growth factor receptor) inhibitors, MTKI (multi target kinase inhibitors), mTOR inhibitors) for example flavoperidol, imatinib mesylate, erlotinib, gefitinib, dasatinib, lapatinib, lapatinib ditosylate, sorafenib, sunitinib, sunitinib maleate, temsirolimus;
- farnesyltransferase inhibitors for example tipifarnib;
- histone deacetylase (HDAC) inhibitors for example sodium butyrate, suberoylanilide hydroxamide acid (SAHA), depsipeptide (FR 901228), NVP-LAQ824, R306465, JNJ-26481585, trichostatin A, vorinostat;
- Inhibitors of the ubiquitin-proteasome pathway for example PS-341, MLN 0.41 or bortezomib;
- Yondelis;
- Telomerase inhibitors for example telomestatin;
- Matrix metalloproteinase inhibitors for example batimastat, marimastat, prinostat or metastat.
- Recombinant interleukins for example aldesleukin, denileukin diftitox, interferon alfa 2a, interferon alfa 2b, peginterferon alfa 2b
- MAPK inhibitors
- Retinoids for example alitretinoin, bexarotene, tretinoin
- Arsenic trioxide
- Asparaginase
- Steroids for example dromostanolone propionate, megestrol acetate, nandrolone (decanoate, phenpropionate), dexamethasone
- Gonadotropin releasing hormone agonists or antagonists for example abarelix, goserelin acetate, histrelin acetate, leuprolide acetate
- Thalidomide, lenalidomide
- Mercaptopurine, mitotane, pamidronate, pegademase, pegaspargase, rasburicase
- BH3 mimetics for example ABT-737
- MEK inhibitors for example PD98059, AZD6244, CI-1040
- colony-stimulating factor analogs for example filgrastim, pegfilgrastim, sargramostim; erythropoietin or analogues thereof (e.g. darbepoetin alfa); interleukin 11; oprelvekin; zoledronate, zoledronic acid; fentanyl; bisphosphonate; palifermin.

The term "platinum coordination compound" is used herein to denote any tumour cell growth inhibiting platinum coordination compound which provides platinum in the form of an ion. The platinum coordination compound is advantageously administered in a dosage of 1 to 500 mg per square meter (mg/m$^2$) of body surface area, for example 50 to 400 mg/m$^2$, particularly for cisplatin in a dosage of about 75 mg/m$^2$ and for carboplatin in about 300 mg/m$^2$ per course of treatment.

The term "taxane compounds" indicates a class of compounds having the taxane ring system and related to or derived from extracts from certain species of yew (Taxus) trees. The taxane compound is advantageously administered in a dosage of 50 to 400 mg per square meter (mg/m$^2$) of body surface area, for example 75 to 250 mg/m$^2$, particularly for paclitaxel in a dosage of about 175 to 250 mg/m$^2$ and for docetaxel in about 75 to 150 mg/m$^2$ per course of treatment.

The term "topoisomerase inhibitors" is used to indicate enzymes that are capable of altering DNA topology in eukaryotic cells. They are critical for important cellular functions and cell proliferation. There are two classes of topoisomerases in eukaryotic cells, namely type I and type II. Topoisomerase I is a monomeric enzyme of approximately 100,000 molecular weight. The enzyme binds to DNA and introduces a transient single-strand break, unwinds the double helix (or allows it to unwind) and subsequently reseals the break before dissociating from the DNA strand. Topisomerase II has a similar mechanism of action which involves the induction of DNA strand breaks or the formation of free radicals.

The term "camptothecin compounds" is used to indicate compounds that are related to or derived from the parent camptothecin compound which is a water-insoluble alkaloid derived from the Chinese tree Camptothecin acuminata and the Indian tree Nothapodytes foetida. The camptothecin compound is advantageously administered in a dosage of 0.1 to 400 mg per square meter ($mg/m^2$) of body surface area, for example 1 to 300 $mg/m^2$, particularly for irinotecan in a dosage of about 100 to 350 $mg/m^2$ and for topotecan in about 1 to 2 $mg/m^2$ per course of treatment.

The term "podophyllotoxin derivatives" is used to indicate compounds that are related to or derived from the parent podophyllotoxin, which is extracted from the mandrake plant. The anti-tumour podophyllotoxin derivative is advantageously administered in a dosage of 30 to 300 mg per square meter ($mg/m^2$) of body surface area, for example 50 to 250 $mg/m^2$, particularly for etoposide in a dosage of about 35 to 100 $mg/m^2$ and for teniposide in about 50 to 250 $mg/m^2$ per course of treatment.

The term "anti-tumour vinca alkaloids" is used to indicate compounds that are related to or derived from extracts of the periwinkle plant (Vinca rosea). The anti-tumour vinca alkaloid is advantageously administered in a dosage of 2 to 30 mg per square meter ($mg/m^2$) of body surface area, particularly for vinblastine in a dosage of about 3 to 12 $mg/m^2$, for vincristine in a dosage of about 1 to 2 $mg/m^2$, and for vinorelbine in dosage of about 10 to 30 $mg/m^2$ per course of treatment.

The anti-tumour nucleoside derivative is advantageously administered in a dosage of 200 to 2500 mg per square meter ($mg/m^2$) of body surface area, for example 700 to 1500 $mg/m^2$, particularly for 5-FU in a dosage of 200 to 500 $mg/m^2$, for gemcitabine in a dosage of about 800 to 1200 $mg/m^2$ and for capecitabine in about 1000 to 2500 $mg/m^2$ per course of treatment.

The term "alkylating agents" encompass a diverse group of chemicals that have the common feature that they have the capacity to contribute, under physiological conditions, alkyl groups to biologically vital macromolecules such as DNA. With most of the more important agents such as the nitrogen mustards and the nitrosoureas, the active alkylating moieties are generated in vivo after complex degradative reactions, some of which are enzymatic. The most important pharmacological actions of the alkylating agents are those that disturb the fundamental mechanisms concerned with cell proliferation in particular DNA synthesis and cell division. The capacity of alkylating agents to interfere with DNA function and integrity in rapidly proliferating tissues provides the basis for their therapeutic applications and for many of their toxic properties. The alkylating agents such as nitrogen mustard or nitrosourea is advantageously administered in a dosage of 100 to 500 mg per square meter ($mg/m^2$) of body surface area, for example 120 to 200 $mg/m^2$, particularly for cyclophosphamide in a dosage of about 100 to 500 $mg/m^2$, for chlorambucil in a dosage of about 0.1 to 0.2 mg/kg, for carmustine in a dosage of about 150 to 200 $mg/m^2$, and for lomustine in a dosage of about 100 to 150 $mg/m^2$ per course of treatment.

The term "anti-tumour anthracycline derivatives" comprise antibiotics obtained from the fungus Strep. peuticus var. caesius and their derivatives, characterised by having a tetracycline ring structure with an unusual sugar, daunosamine, attached by a glycosidic linkage. The anti-tumour anthracycline derivative is advantageously administered in a dosage of 10 to 75 mg per square meter ($mg/m^2$) of body surface area, for example 15 to 60 $mg/m^2$, particularly for doxorubicin in a dosage of about 40 to 75 $mg/m^2$, for daunorubicin in a dosage of about 25 to 45 $mg/m^2$, and for idarubicin in a dosage of about 10 to 15 $mg/m^2$ per course of treatment.

Amplification of the human epidermal growth factor receptor 2 protein (HER 2) in primary breast carcinomas has been shown to correlate with a poor clinical prognosis for certain patients. Trastuzumab is a highly purified recombinant DNA-derived humanized monoclonal IgG1 kappa antibody that binds with high affinity and specificity to the extracellular domain of the HER2 receptor.

Many breast cancers have estrogen receptors and growth of these tumours can be stimulated by estrogen. The terms "estrogen receptor antagonists" and "selective estrogen receptor modulators" are used to indicate competitive inhibitors of estradiol binding to the estrogen receptor (ER). Selective estrogen receptor modulators, when bound to the ER, induces a change in the three-dimensional shape of the receptor, modulating its binding to the estrogen responsive element (ERE) on DNA.

In postmenopausal women, the principal source of circulating estrogen is from conversion of adrenal and ovarian androgens (androstenedione and testosterone) to estrogens (estrone and estradiol) by the aromatase enzyme in peripheral tissues. Estrogen deprivation through aromatase inhibition or inactivation is an effective and selective treatment for some postmenopausal patients with hormone-dependent breast cancer.

The term "differentiating agents" encompass compounds that can, in various ways, inhibit cell proliferation and induce differentiation. Vitamin D and retinoids are known to play a major role in regulating growth and differentiation of a wide variety of normal and malignant cell types. Retinoic acid metabolism blocking agents (RAMBA's) increase the levels of endogenous retinoic acids by inhibiting the cytochrome P450-mediated catabolism of retinoic acids.

DNA methylation changes are among the most common abnormalities in human neoplasia. Hypermethylation within the promoters of selected genes is usually associated with inactivation of the involved genes. The term "DNA methyl transferase inhibitors" is used to indicate compounds that act through pharmacological inhibition of DNA methyl transferase and reactivation of tumour suppressor gene expression.

The term "kinase inhibitors" comprises potent inhibitors of kinases that are involved in cell cycle progression and programmed cell death (apoptosis).

The term "farnesyltransferase inhibitors" is used to indicate compounds that were designed to prevent farnesylation of Ras and other intracellular proteins. They have been shown to have effect on malignant cell proliferation and survival.

The term "histone deacetylase inhibitor" or "inhibitor of histone deacetylase" is used to identify a compound, which is capable of interacting with a histone deacetylase and inhibiting its activity, more particularly its enzymatic activity. Inhibiting histone deacetylase enzymatic activity means reducing the ability of a histone deacetylase to remove an acetyl group from a histone.

The term "other inhibitors of the ubiquitin-proteasome pathway" is used to identify compounds that inhibit the targeted destruction of cellular proteins in the proteasome, including cell cycle regulatory proteins.

The term "telomerase inhibitor" refers to compounds which target, decrease or inhibit the activity of telomerase, especially compounds which inhibit the telomerase receptor.

The term "matrix metalloproteinase inhibitor" includes but is not limited to, collagen peptidomimetic and non-peptidomimetic inhibitors.

The present invention also relates to a combination according to the invention for use in medical therapy for example for inhibiting the growth of tumour cells.

The present invention also relates to a combination according to the invention for inhibiting the growth of tumour cells.

The present invention also relates to a method of inhibiting the growth of tumour cells in a human subject which comprises administering to the subject an effective amount of a combination according to the invention.

This invention further provides a method for inhibiting the abnormal growth of cells, including transformed cells, by administering an effective amount of a combination according to the invention.

The other medicinal agent and the compound of formula (I) with tubulin binding properties may be administered simultaneously (e.g. in separate or unitary compositions) or sequentially in either order. In the latter case, the two compounds will be administered within a period and in an amount and manner that is sufficient to ensure that an advantageous or synergistic effect is achieved. It will be appreciated that the preferred method and order of administration and the respective dosage amounts and regimes for each component of the combination will depend on the particular other medicinal agent and compound of formula (I) with tubulin binding properties being administered, their route of administration, the particular tumour being treated and the particular host being treated. The optimum method and order of administration and the dosage amounts and regime can be readily determined by those skilled in the art using conventional methods and in view of the information set out herein.

Those skilled in the art could easily determine the effective amount from the test results presented hereinafter. In general it is contemplated that an effective amount would be from 0.001 mg/kg to 100 mg/kg body weight, and in particular from 0.005 mg/kg to 10 mg/kg body weight. It may be appropriate to administer the required dose as two, three, four or more sub-doses at appropriate intervals throughout the day. Said sub-doses may be formulated as unit dosage forms, for example, containing 0.05 to 500 mg, and in particular 0.1 mg to 200 mg of active ingredient per unit dosage form.

The exact dosage and frequency of administration depends on the particular compound of formula (I) used, the particular condition being treated, the severity of the condition being treated, the age, weight, sex, extent of disorder and general physical condition of the particular patient as well as other medication the individual may be taking, as is well known to those skilled in the art. Furthermore, it is evident that said effective daily amount may be lowered or increased depending on the response of the treated subject and/or depending on the evaluation of the physician prescribing the compounds of the instant invention.

Depending on the mode of administration, the pharmaceutical composition will preferably comprise from 0.05 to 99% by weight, more preferably from 0.1 to 70% by weight, even more preferably from 0.1 to 50% by weight of the active ingredient, and, from 1 to 99.95% by weight, more preferably from 30 to 99.9% by weight, even more preferably from 50 to 99.9% by weight of a pharmaceutically acceptable carrier, all percentages being based on the total weight of the composition.

The following examples illustrate the present invention.

EXPERIMENTAL PART

Hereinafter, "BuLi" is defined as n-butyl-lithium, "DCM" is defined as dichloromethane, "DIPE" is defined as diisopropyl ether, "Et$_2$O" is defined as diethylether, 'DMSO' is defined as dimethylsulfoxide, "EtOAc" is defined as ethyl acetate, "EtOH" is defined as ethanol, "MeOH" is defined as methanol, "TFA" is defined as trifluoroacetic acid and "THF" is defined as tetrahydrofuran.

Of some compounds having 1 chiral center the absolute stereochemical configuration of the stereogenic carbon atom therein was not experimentally determined. In those cases the stereochemically isomeric form which was first isolated is designated as "enantiomer A" and the second as "enantiomer B", without further reference to the actual stereochemical configuration. However, said actual stereochemical configuration of "enantiomer A" and "enantiomer B" forms can unambiguously be characterized by a person skilled in the art, using art-known methods such as, for example, X-ray diffraction. The isolation method is described in detail below.

Of some compounds having 2 chiral centers the absolute stereochemical configuration of the stereogenic carbon atoms therein was not experimentally determined. In those cases the mixture of 2 enantiomers (e.g. mixture of R,R-enantiomer and S,S-enantiomer or mixture of R,S-enantiomer and S,R-enantiomer) which was first isolated is designated as "dia A" and the second as "dia B", without further reference to the actual stereochemical configuration. However, said actual stereochemical configuration of "dia A" and "dia B" forms can unambiguously be characterized by a person skilled in the art, using art-known methods such as, for example first separating the mixture into the composing enantiomers and then determining the stereoconfiguration of the enantiomers with, for example. X-ray diffraction. The isolation method is described in detail below.

A. Preparation of the Intermediate Compounds

Example A1 a) Preparation of Intermediate 1

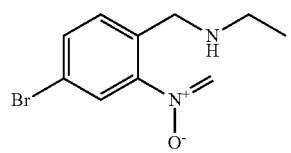

A solution of 4-bromo-1-(bromomethyl)-2-nitro-benzene (0.231 mol) in MeOH (186 ml) was added dropwise at 5° C. to a solution of ethanamine 70% in H$_2$O (1.155 mol) in MeOH (93 ml). The mixture was refluxed for 1 hour, the solvent was evaporated and the residue poured out into water and extracted with DCM. The organic layer was separated, dried (MgSO$_4$), filtered and the solvent was evaporated. The residue (68 g) was purified by column chromatography over silica gel (15-40 μm) (eluent: DCM/MeOH 98/2). The pure fractions were collected and the solvent was evaporated, yielding 30 g (50%) of intermediate 1.

b) Preparation of Intermediate 2

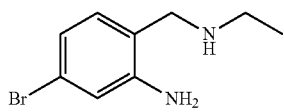

Platinum oxide (0.008 mol) then zinc acetate hydrate (0.110 mol) were added at room temperature to a solution of intermediate 1 (0.057 mol) in MeOH (200 ml) under $N_2$ flow. The mixture was hydrogenated overnight under a 2 bar pressure, then filtered over celite. Celite was washed with MeOH. The filtrate was evaporated till dryness, the crude product was dissolved in EtOAc, poured out into water and basified with potassium carbonate. The organic layer was separated, dried ($MgSO_4$), filtered and the solvent was evaporated, yielding 13.2 g (100%) of intermediate 2.

c) Preparation of Intermediate 3

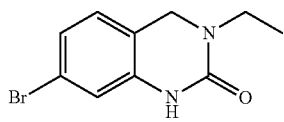

A mixture of intermediate 2 (0.057 mol) and di-1H-imidazol-1-yl-methanone (0.069 mol) in THF (200 ml) was stirred and refluxed for 3 hours, poured out into cold water and extracted with EtOAc. The organic layer was separated, dried ($MgSO_4$), filtered and the solvent was evaporated. The residue was washed with $CH_3CN$/DCM. The precipitate was filtered off and dried, yielding 11.20 g (76%) of intermediate 3.

d) Preparation of Intermediate 4

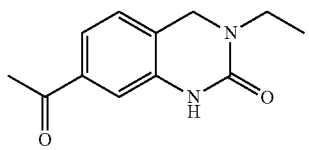

BuLi (1.6M in hexane, 7.6 ml, 0.0121 mol) was added dropwise at −78° C. to a solution of intermediate 3 (0.0055 mol) in THF (15 ml) under $N_2$ flow. The mixture was stirred at −78° C. for 1 hour. A solution of N-methoxy-N-methyl-acetamide (0.00823 mol) in THF (4 ml) was added. The mixture was stirred at −70° C. for 1 hour, then stirred at room temperature for 4 hours, poured out into water and extracted with EtOAc. The organic layer was separated, dried ($MgSO_4$), filtered and the solvent was evaporated. The residue (2.4 g) was purified by column chromatography over silica gel (15-40 μm) (eluent: cyclohexane/EtOAc 50/50). The pure fractions were collected and the solvent was evaporated. The residue was crystallized from DIPE. The precipitate was filtered off and dried, yielding 0.360 g (30%) of intermediate 4, melting point 190° C.

e) Preparation of Intermediate 5

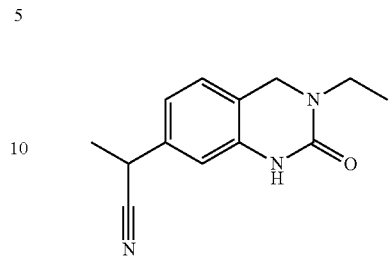

2-methyl-2-propanol, potassium salt (0.0076 mol) was added portionwise at 15° C. to a solution of 1-[(isocyanomethyl)sulfonyl]-4-methyl-benzene (0.0016 mol) in DMSO (4 ml) under $N_2$ flow. MeOH (0.4 ml) was added dropwise. The mixture was stirred for 15 minutes. Intermediate 4 (0.0016 mol) was added portionwise. The mixture was stirred for 45 minutes, poured out into water and extracted with DCM. The organic layer was washed with saturated NaCl, dried ($MgSO_4$), filtered and the solvent was evaporated. The residue (0.7 g) was purified by column chromatography over silica gel (15-40 μm) (eluent: DCM/MeOH 98/2). The pure fractions were collected and the solvent was evaporated, yielding 0.333 g (88%) of intermediate 5, melting point 119° C.

Example A2 a) Preparation of Intermediate 6

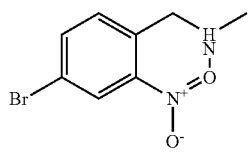

A solution of 4-bromo-1-(bromomethyl)-2-nitro-benzene (0.037 mol) in MeOH (26 ml) was added dropwise at 5° C. to a solution of methanamine 40% in $H_2O$ (0.186 mol) in MeOH (13 ml). The mixture was refluxed for 1 hour, the solvent was evaporated and the residue poured out into water and extracted with DCM. The organic layer was separated, dried ($MgSO_4$), filtered and the solvent was evaporated. The residue was purified by column chromatography over silica gel (15-40 μm) (eluent: DCM/MeOH 96/4). The pure fractions were collected and the solvent was evaporated, yielding 3 g (33%) of intermediate 6.

b) Preparation of Intermediate 7

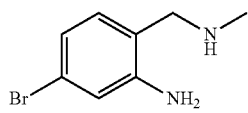

Platinum oxide (0.0022 mol) then zinc acetate hydrate (0.0285 mol) were added at room temperature to a solution of intermediate 6 (0.015 mol) in MeOH (600 ml) under $N_2$ flow.

c) Preparation of Intermediate 8a

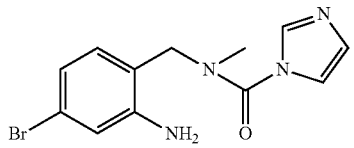

A mixture of intermediate 7 (0.014 mol) and di-1H-imidazol-1-yl-methanone (0.0174 mol) in THF (40 ml) was stirred and refluxed for 3 hours, poured out into cold water and extracted with DCM. The organic layer was separated, dried (MgSO₄), filtered and the solvent was evaporated. The residue was crystallized, the precipitate was filtered off and dried, yielding 3 g (70%) of intermediate 8a.

d) Preparation of Intermediate 8b

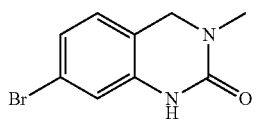

Sodium hydride (60% in oil, 0.0136 mol) is added portionwise to a solution of intermediate 8a in THF (30 ml) at 5° C. under N₂ flow. The mixture was stirred at 5° C. for 1 hour, poured out onto water and extracted with DCM. The organic layer was separated, dried (MgSO₄), filtered and the solvent was evaporated. The residue was crystallized with DIPE, the precipitate was filtered off and dried, yielding 1.2 g (55%) of intermediate 8b.

e) Preparation of Intermediate 8c

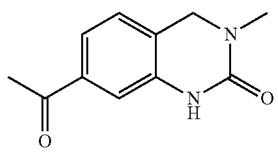

BuLi (1.6M in hexane, 6.85 ml, 0.0109 mol) was added dropwise at −78° C. to a solution of intermediate 8b (0.0050 mol) in THF (15 ml) under N₂ flow. The mixture was stirred at −78° C. for 1 hour. A solution of N-methoxy-N-methyl-acetamide (0.0075 mol) was added. The mixture was stirred at −70° C. for 1 hour, then stirred at room temperature for 15 hours, poured out into water and extracted with EtOAc. The organic layer was separated, dried (MgSO₄), filtered and the solvent was evaporated. The residue (2 g) was purified by column chromatography over silica gel (15-40 μm) (eluent: DCM/MeOH 96/4). The pure fractions were collected and the solvent was evaporated, yielding 0.274 g (27%) of intermediate 8c.

f) Preparation of Intermediate 8d

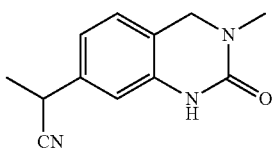

2-methyl-2-propanol, potassium salt (0.0061 mol) was added portionwise at 15° C. to a solution of 1-[(isocyanomethyl)sulfonyl]-4-methyl-benzene (0.0031 mol) in DMSO (3 ml) under N₂ flow. MeOH (0.3 ml) was added dropwise. The mixture was stirred for 15 minutes. Intermediate 8c (0.00134 mol) was added portionwise. The mixture was stirred for 20 minutes, poured out into water and extracted with DCM. The organic layer was washed with saturated NaCl, dried (MgSO₄), filtered and the solvent was evaporated. The residue (0.7 g) was purified by column chromatography over silica gel (15-40 μm) (eluent: DCM/MeOH 96/4). The pure fractions were collected and the solvent was evaporated yielding 0.117 g (41%) of intermediate 8d.

g) Preparation of Intermediate 9

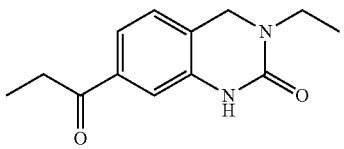

BuLi (0.080 mol; 50 ml, 1.6 M in hexane) was added dropwise to a mixture of intermediate 3 (0.020 mol) in THF anhydrous (24 ml) at −78° C. under a nitrogen flow. The mixture was stirred at −78° C. for 45 minutes. A solution of N-methoxy-N-methyl-propanamide (0.100 mol) in THF anhydrous (1 ml) was added dropwise and the resulting reaction mixture stirred at −70° C. for 2 hours and then allowed to warm up to room temperature. The mixture was stirred at room temperature overnight. Water was added and the mixture was extracted with EtOAc. The organic layer was dried (MgSO₄), filtered and evaporated to dryness. The residue was purified by column chromatography (eluent: Petroleum ether/EtOAc=4:1) The product fractions were collected and the solvent was evaporated, yielding 1.1 g of (23%) of intermediate 9.

h) Preparation of Intermediate 10

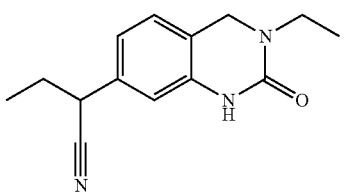

To a solution of 1-[(isocyanomethyl)sulfonyl]-4-methyl-benzene (0.01114 mol) in DMSO (12 ml) under nitrogen at 10° C., were added 2-methyl-2-propanol, potassium salt (0.0223 mol) and MeOH (1.2 ml). The mixture was stirred at 10° C. for 15 minutes, then intermediate 9 (0.00474 mol) was added portionwise. The reaction mixture was stirred at 10° C. for 45 minutes, then poured out onto ice-water, then extracted with EtOAc. The organic layer was separated, dried (MgSO$_4$), filtered and the filtrate's solvent was evaporated. The residue was purified by prep. TLC (eluent: EtOAc/Petroleum=1:1). The pure fractions were collected and the solvent was evaporated, yielding 0.6 g (52%) of intermediate 10.

Example A3 a) Preparation of Intermediate 11

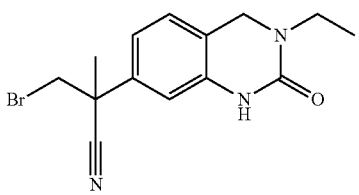

BuLi (1.6M in hexane, 0.004798 mol) was added dropwise to a mixture of diisopropylamine (0.004798 mol) in THF (4 ml) at −20° C. under N$_2$. The mixture was stirred 20 minutes at −20° C. and cooled at −70° C. A solution of intermediate 5 (0.002181 mol) in THF (8 ml) was added dropwise at −70° C. and stirred during 1 hour. A solution of dibromomethane (0.002835 mol) was added dropwise at −70° C. and stirred at −70° C. during 1 hour then 1 hour at 0° C. The reaction mixture was poured out into ice water and EtOAc was added. The organic layer was separated, washed with brine, dried (MgSO$_4$), filtered and the solvent was evaporated. The residue was purified by column chromatography over silica gel (15/40 μm) (eluent: DCM 100 to DCM 98/MeOH 2). The pure fractions were collected and the solvent was evaporated. The residue (0.556 g) was crystallized from Et$_2$O/DIPE, filtered and dried under vacuum, yielding 0.500 g (71%) of intermediate 11, melting point 160° C.

b) Preparation of Intermediate 12

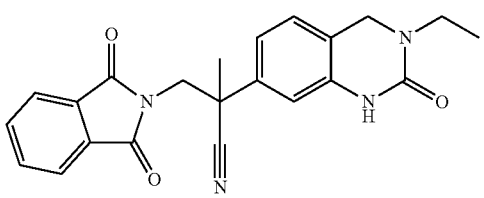

A solution of intermediate 11 (0.001241 mol), potassium phthalimide (0.001862 mol) in N-dimethylformamide (10 ml) was heated at 150° C. during 45 minutes under microwaves. The reaction mixture was cooled to room temperature and poured out into ice water. EtOAc was added and the organic layer was separated, washed with brine, dried (MgSO$_4$), filtered and the solvent was evaporated. The residue was triturated from Et$_2$O/CH$_3$CN, filtered and dried under vacuum, yielding 0.380 g (55%) of intermediate 12, melting point 208° C.

c) Preparation of Intermediate 13

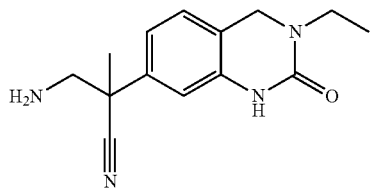

Hydrazine monohydrate (0.009783 mol) was added dropwise to a solution of intermediate 12 (0.000978 mol) in EtOH (20 ml) at room temperature. The mixture was heated at 80° C. during 4 hours. The reaction mixture was cooled to room temperature and the precipitate was filtered and the filtrate was poured out into ice water then EtOAc was added. The organic layer was separated, dried (MgSO$_4$), filtered and the solvent was evaporated. The product was crystallized from Et$_2$O, filtered and dried under vacuum, yielding 0.180 g (71%) of intermediate 13.

Example A4

Preparation of Intermediate 14

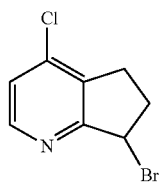

Dibromotriphenyl-phosphorane (0.004 mol) was added to a solution of 4-chloro-6,7-dihydro-5H-Cyclopenta[b]pyridin-7-ol (0.002 mol) in acetonitrile (6 ml). The mixture was stirred for 3 hours, quenched with potassium carbonate 10% and extracted with EtOAc. The organic layer was separated, dried (MgSO$_4$), filtered and the solvent was evaporated till dryness. The residue (1.6 g) was purified by column chromatography over silica gel (15-40 μm) (eluent DCM 100). The pure fractions were collected and the solvent was evaporated till dryness, yielding 0.31 g (67%) of intermediate 14.

B. Preparation of the Final Compounds

Example B1

Preparation of Compound 1

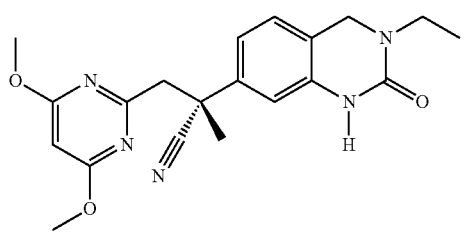

enantiomer B

BuLi (0.0048 mol) was added dropwise to a mixture of diisopropylamine (0.0048 mol) in THF (6 ml) at −20° C. under N$_2$ flow. The mixture was stirred at −20° C. for 20 minutes, cooled to −70° C. A solution of intermediate 5 (0.0022 mol) in THF (3 ml) was added. The mixture was stirred at −70° C. for 45 minutes. 2-(chloromethyl)-4,6-dimethoxy-pyrimidine (0.0033 mol) was added. The mixture was stirred at −70° C. for 2 hours and at 10° C. for 2 hours. Water was added. The mixture was extracted with EtOAc. The organic layer was separated, dried over magnesium sulfate, filtered, and the solvent was evaporated. The residue (1.24 g) was purified by column chromatography over silica gel (15-40 μm) (eluent: Toluene/isopropanol/NH$_4$OH 97/3/0.1). The pure fractions were collected and the solvent was evaporated. The racemic mixture (0.5 g, 60%) was separated into two enantiomers by column chromatography over chiral phase (eluent: MeOH 100%). Two fractions were collected and the solvent was evaporated, yielding 0.26 g of F1 and 0.22 g of F2. F2 was crystallized from DIPE. The precipitate was filtered off and dried under vacuum, yielding 0.1 g (12%) of compound 1 (enantiomer B), melting point 95° C., $[\alpha]_D^{20}$=+28.97 (DMF; c=0.32).

Example B2

Preparation of Compound 2

BuLi (1.6M in hexane, 0.00295 mol) was added dropwise to a mixture of diisopropylamine (0.00295 mol) in THF (2 ml), stirred at −20° C. under a nitrogen flow. The mixture was stirred at −20° C. for 20 min and cooled to −70° C. A solution of intermediate 10 (0.00123 mol) in THF (2 ml) was added dropwise and the resulting mixture was stirred at −70° C. for 45 minutes. A solution of 3-(bromomethyl)-benzonitrile (0.00185 mol) in THF (1 ml) was added. The resultant reaction mixture was stirred for 2 hours at −70° C. and allowed to warm up to room temperature. Water was added and the mixture was extracted with EtOAc. The organic layer was separated, dried over magnesium sulfate, filtered and the filtrate's solvent was evaporated. The residue was purified by chromatography over silica gel (eluent: H$_2$O (0.1% TFA) CH$_3$CN (0.1% TFA)). The pure fraction was collected and 10 ml of a 10% aqueous sodiumcarbonate solution was added. The resulting mixture was extracted with DCM. The separated organic layer was washed with water, dried (MgSO$_4$) and filtered. The desired product was obtained by lyophilization as white powder, yielding 0.06 g (15%) of compound 2.

Example B3

Preparation of compounds 3 and 4 compound 3 enantiomer A and compound 4 enantiomer B

BuLi (1.6M in hexane, 0.024 mol) was added dropwise at −20° C. to a solution of diisopropylamine (0.024 mol) in THF (20 ml) under N$_2$ flow. The mixture was stirred at −20° C. for 20 minutes, then cooled to −70° C. A solution of intermediate 5 (0.01 mol) in THF (10 ml) was added. The mixture was stirred at −70° C. for 45 minutes. A solution of (bromomethyl)-benzene (0.0163 mol) in THF (5 ml) was added. The mixture was stirred at −70° C. for 2 hours, then stirred at 10° C. for 2 hours. Water was added. The mixture was extracted with EtOAc. The organic layer was separated, dried (MgSO$_4$), filtered and the solvent was evaporated. The residue (4.26 g) was purified by column chromatography over silica gel (eluent: DCM/MeOH/NH$_4$OH 99/1/0.1). The pure fractions were collected and the solvent was evaporated. The racemic mixture (2.6 g, 75%) was separated by chiral chromatography (eluent: MeOH 100). Two fractions were collected and the solvent was evaporated, yielding 1.1 g F1 and 1.1 g F2. F1 was crystallized from DIPE. The precipitate was filtered off and dried, yielding 0.78 g (22%) of compound 3 (enantiomer A), melting point 124° C., $[\alpha]_D^{20}$=+89.2 (DMF; c=0.28). F2 was crystallized from DIPE/isopropanol. The precipitate was filtered off and dried, yielding 0.798 g (23%) of compound 4 (enantiomer B), melting point 124° C., $[\alpha]_D^{20}$=−96.05 (DMF; c=0.29)

Example B4

Preparation of Compounds 5 and 6 compound 5 enantiomer A and compound 6 enantiomer B

BuLi (1.6M, 0.0192 mol) was added dropwise at –20° C. to a solution of diisopropylamine (0.0192 mol) in THF (20 ml) under N₂ flow. The mixture was stirred at –20° C. for 20 minutes, then cooled to –70° C. A solution of intermediate 5 (0.0087 mol) in THF (15 ml) was added. The mixture was stirred at –70° C. for 45 minutes. 3-(bromomethyl)-benzonitrile (0.013 mol) was added. The mixture was stirred at –70° C. for 2 hours, then stirred at 10° C. for 2 hours. Water was added. The mixture was extracted with EtOAc. The organic layer was separated, dried (MgSO₄), filtered and the solvent was evaporated. The residue (4.2 g) was purified by column chromatography over silica gel (eluent: DCM/MeOH/NH₄OH 98/2/0.1). The pure fractions were collected and the solvent was evaporated. The racemic mixture (1.4 g, 47%) was separated by column chromatography over chiral phase (eluent: MeOH 100). Two fractions were collected and the solvent was evaporated, yielding 0.65 g F1 and 0.65 g F2. F1 was crystallized from diethyl ether. The precipitate was filtered off and dried, yielding 0.56 g (18.6%) of compound 5 (enantiomer A), melting point 152° C., $[\alpha]_D^{20}$=+88.92 (DMF; c=0.32). F2 was crystallized from diethyl ether. The precipitate was filtered off and dried, yielding 0.51 g (17%) of compound 6 (enantiomer B), melting point 152° C.; $[\alpha]_D^{20}$=–93.62 (DMF; c=0.28).

Example B5

Preparation of Compound 7

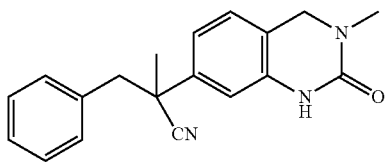

BuLi (0.00119 mol) was added dropwise to a mixture of diisopropylamine (0.00119 mol) in THF (2 ml) at –20° C. under N₂ flow. The mixture was stirred at –20° C. for 20 minutes, cooled to –70° C. A solution of intermediate 8d (0.00054 mol) in THF (2 ml) was added. The mixture was stirred at –70° C. for 45 minutes. Bromomethyl-benzene (0.000815 mol) was added. The mixture was stirred at –70° C. for 2 hours and at 10° C. for 2 hours. Water was added. The mixture was extracted with EtOAc. The organic layer was separated, dried over magnesium sulfate, filtered, and the solvent was evaporated. The residue (0.17 g) was purified by column chromatography over silica gel (15-40 μm) (eluent: DCM/MeOH 99/1). The pure fractions were collected and the solvent was evaporated. The residue was crystallized from DIPE. The precipitate was filtered off and dried, yielding 0.009 g (5%) of compound 7, melting point 210° C.

Example B6 a) Preparation of Compound 8

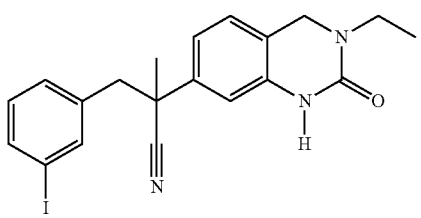

BuLi (1.6M, 0.0009 mol) was added dropwise at –20° C. to a solution of diisopropylamine (0.0009 mol) in THF (1.5 ml) under N₂ flow. The mixture was stirred at –20° C. for 20 minutes, then cooled to –70° C. A solution of intermediate 5 (0.0004 mol) in THF (1.5 ml) was added. The mixture was stirred at –70° C. for 45 minutes. 1-(bromomethyl)-3-iodobenzene (0.0006 mol) was added. The mixture was stirred at –70° C. for 2 hours, then stirred at 10° C. for 2 hours. Water was added. The mixture was extracted with EtOAc. The organic layer was separated, dried (MgSO₄), filtered and the solvent was evaporated. The residue (0.25 g) was purified by column chromatography over silica gel (eluent: DCM/MeOH 99/1). The pure fractions were collected and the solvent was evaporated, yielding 0.104 g (53%) of compound 8, melting point 83° C.

b) Preparation of Compound 9

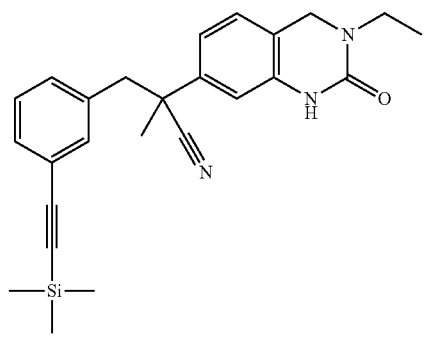

A mixture of compound 8 (0.002 mol), ethynyltrimethylsilane (0.004 mol), copper iodide (0.0001 mol), dichlorobis(triphenylphosphine)-palladium (0.0006 mol) and N-ethylethanamine (0.008 mol) in THF (50 ml) was stirred at 60° C. for 2 hours. Water was added. The organic layer was separated, dried (MgSO₄), filtered and the solvent was evaporated. The residue was purified by flash column chromatography over silica gel. The pure fractions were collected and the solvent was evaporated, yielding 0.45 g (54%) of compound 9.

c) Preparation of Compound 10

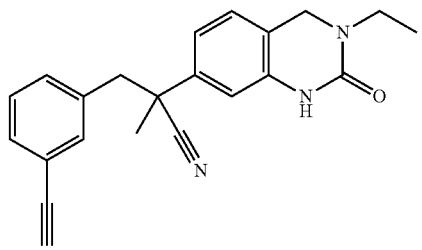

Potassium carbonate (0.003 mol) was added to a solution of compound 9 (0.001 mol) in MeOH (50 ml). The mixture was stirred at room temperature for 2 hours and the solvent was evaporated in vacuo. The residue was purified by prep-HPLC column chromatography. The pure fractions were collected and the solvent was evaporated, yielding 0.03 g (10%) of compound 10, melting point 84.4° C.-102.4° C.

Example B7

Preparation of Compound 11

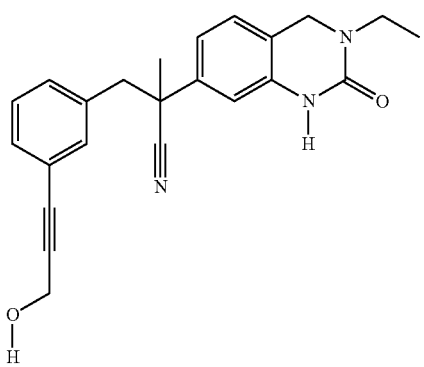

Copper iodide (0.0001 mol) was added portionwise at room temperature to a mixture of compound 8 (0.0006 mol), 2-propyn-1-ol (0.0032 mol) and N-ethylethanamine (0.016 mol) in dioxane dry (8 ml) under $N_2$ flow. The mixture was stirred for 10 minutes under $N_2$ flow. Dichlorobis(triphenylphosphine)-palladium (0.0001 mol) was added portionwise. The mixture was stirred at 80° C. for 5 hours, then cooled to room temperature and poured out into ice water. The residue (0.59 g) was purified by column chromatography over silica gel (15-40 μm) (eluent: DCM/MeOH/$NH_4OH$ 94/6/0.6). The pure fractions were collected and the solvent was evaporated, yielding 0.095 g (40%) of compound 11.

Example B8

Preparation of Compound 12

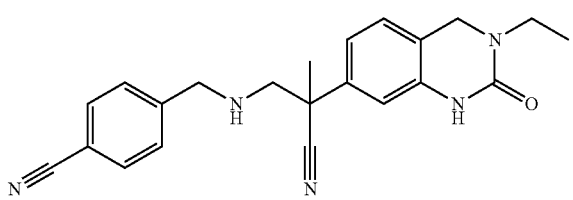

Intermediate 13 (0.000503 mol) was added portionwise to a solution of 4-cyanobenzaldehyde (0.000604 mol), acetic acid (0.20 ml) in 1,2-dichloroethane (4 ml) at room temperature under $N_2$. The reaction mixture was stirred during 1 hour then sodiumtriacetoxyborohydride (0.000654 mol) was added portionwise at room temperature. The reaction mixture was stirred overnight at room temperature. The mixture was poured out into ice water and EtOAc was added. The solution was basified with potassium carbonate powder and the organic layer was separated, dried ($MgSO_4$), filtered and the solvent was evaporated. The residue was purified by column chromatography over silica gel (15/40 μm) (eluent DCM 97/MeOH 3/$NH_4OH$ 0.5). The pure fractions were collected and the solvent was evaporated, yielding 0.045 g (24%) of compound 12.

Example B9

Preparation of Compounds 13 and 14

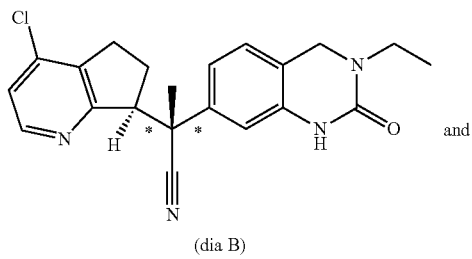

compound 13

(dia B)

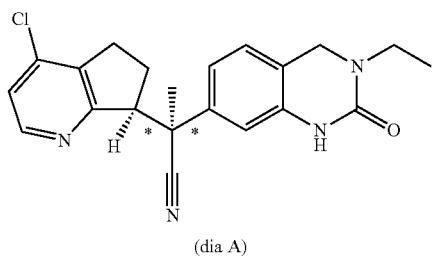

compound 14

(dia A)

BuLi (1.6 M in hexane, 0.002984 mol) was added dropwise to a mixture of diisopropylamine (0.002984 mol) in THF (2 ml) at −20° C. under $N_2$. The mixture was stirred 20 minutes at −20° C. and cooled at −70° C. A solution of intermediate 5 (0.001356 mol) in THF (3 ml) was added dropwise at −70° C. and stirred during 1 hour. A solution of intermediate 14 (0.001763 mol) in THF (2 ml) was added dropwise at −70° C. and stirred at −70° C. during 1 hour then 1 hour at 0° C. The reaction mixture was poured out into ice water and EtOAc was added. The organic layer was separated, washed with brine, dried ($MgSO_4$), filtered and the solvent was evaporated. The residue was purified by supercritical fluid chromatography (eluent: $CO_2$ 90/MeOH 10/isopropanol 0.50). Two fractions were collected and the solvent was evaporated, yielding 0.043 g (8%) of compound 14 (dia A) and 0.170 g (32%) of compound 13 (dia B).

Compound 13 was crystallized from $E_{t2}O$, filtered and dried under vacuum at 50° C., yielding 0.135 g (26%) of compound 13 (dia B), melting point 226° C.
*relative configurations Example B10

Preparation of Compound 15

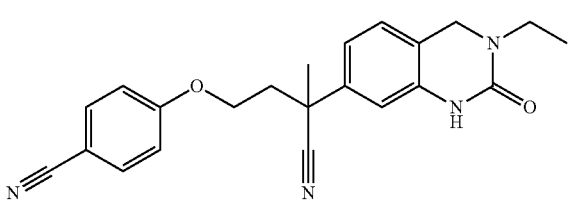

BuLi (1.6M in hexane, 0.001919 mol) was added dropwise to a mixture of diisopropylamine (0.001919 mol) in THF (3 ml) at −20° C. under N₂. The mixture was stirred 20 minutes at −20° C. and cooled at −70° C. A solution of intermediate 5 (0.000872) in THF (2 ml) was added dropwise at −70° C. and stirred during 1 hour at −70° C. A solution of 4-(2-bromoethoxy)-benzonitrile (0.001134 mol) in THF (2 ml) was added dropwise at −70° C. and stirred at −70° C. during 1 hour then 1 hour at 0° C. The reaction mixture was poured out into ice water and EtOAc was added. The organic layer was separated, washed with brine, dried (MgSO₄), filtered and the solvent was evaporated. The residue was purified by super-critical fluid chromatography (Eluent: CO₂ 88/MeOH 12/2-propylamine 0.5). The fractions were collected and the solvent was evaporated. The residue (0.101 g) was purified by column chromatography over silica gel (eluent DCM 100 to DCM 96/MeOH 4/NH₄OH 0.4). The pure fractions were collected and the solvent was evaporated, yielding 0.078 g (23%) of compound 15.

Table F-1 lists the compounds that were prepared according to one of the above Examples.

TABLE F-1

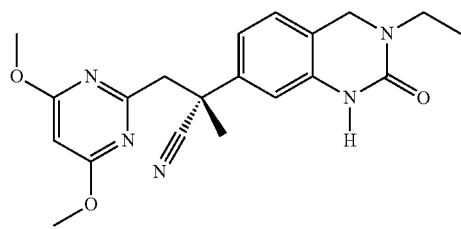

Co. No. 1; Ex. [B1];
enantiomer B; mp. 95° C.

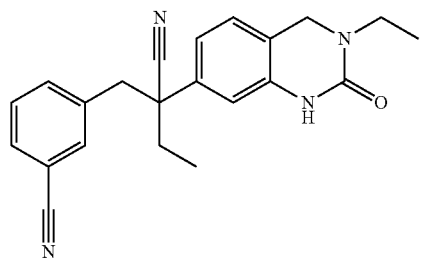

Co. No. 2; Ex. [B2]

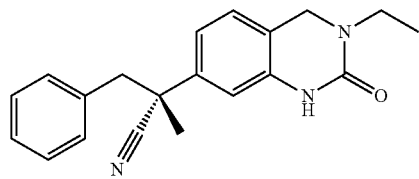

enantiomer A; Co. No. 3;
Ex. [B3]; mp. 124° C.

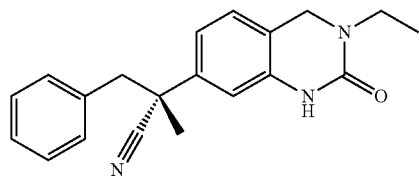

enatiomer B; Co. No. 4;
Ex. [B3]; mp. 124° C.

TABLE F-1-continued

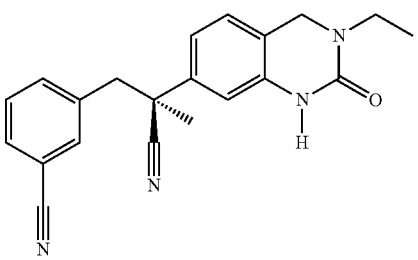

Co. No. 5; Ex. [B4];
mp. 152° C.

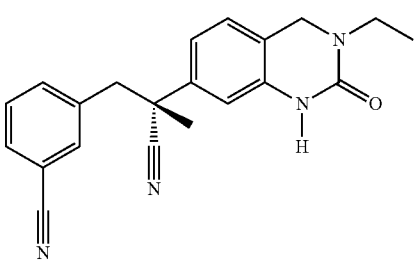

Co. No. 6; Ex. [B4];
mp. 124° C.

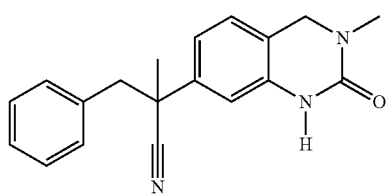

Co. No. 7; Ex. [B5];
mp. 210° C.

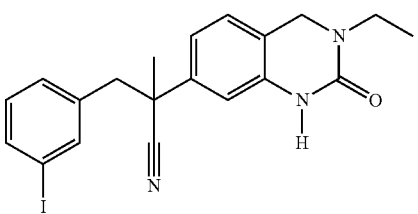

Co. No. 8; Ex. [B6a];
mp. 83° C.

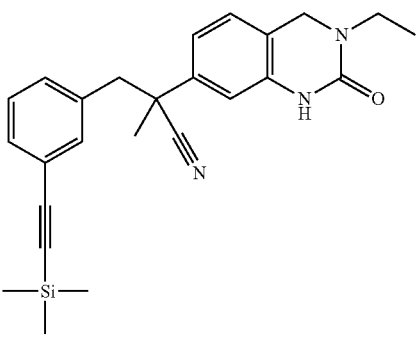

Co. No. 9; Ex. [B6b];

TABLE F-1-continued
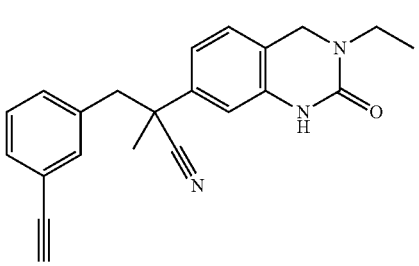
Co. No. 10; Ex. [B6c];
mp. 84.4-102.4° C.
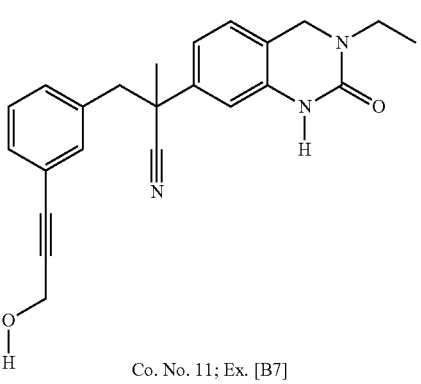
Co. No. 11; Ex. [B7]
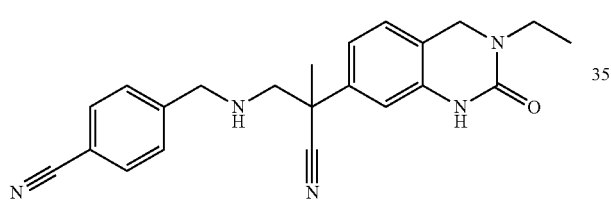
Co. No. 12; Ex. [B8]
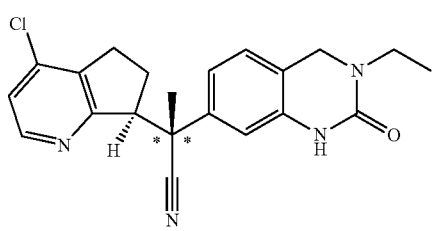
(Dia B); Co. No. 13;
Ex. [B9]; mp. 226° C.
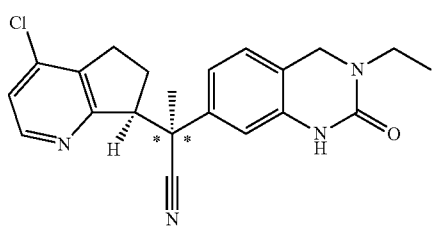
(Dia A); Co. No. 14;
Ex. [B9];
TABLE F-1-continued
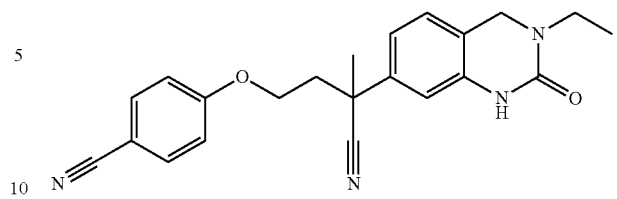
Co. No. 15; Ex. [B10]
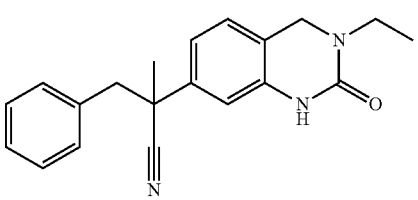
Co. No. 16; Ex. [B1];
mp. 120° C.
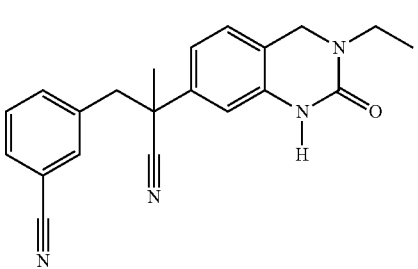
Co. No. 17; Ex. [B1];
mp. 157° C.
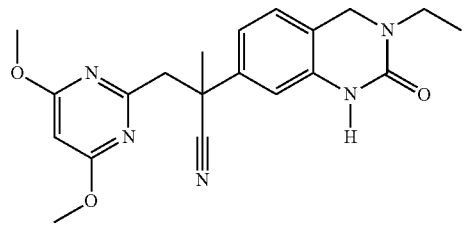
Co. No. 18; Ex. [B1];
mp. 174° C.
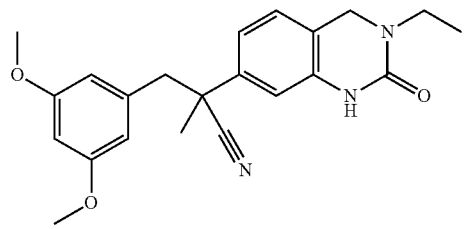
Co. No. 19; Ex. [B1]

TABLE F-1-continued
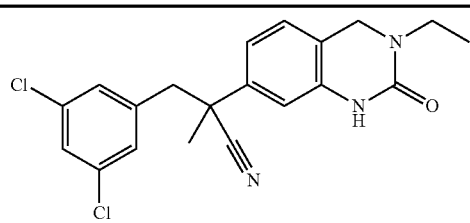
Co. No. 20; Ex. [B1]
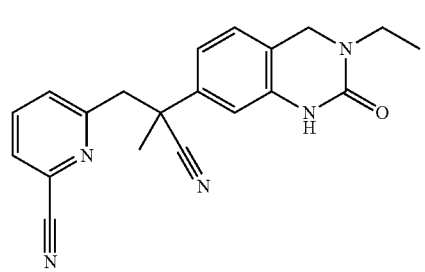
Co. No. 21; Ex. [B1];
mp. 75.2°-80.2° C.
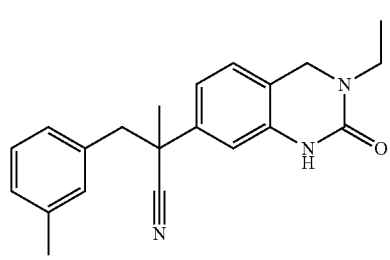
Co. No. 22; Ex. [B1];
mp. 133° C.
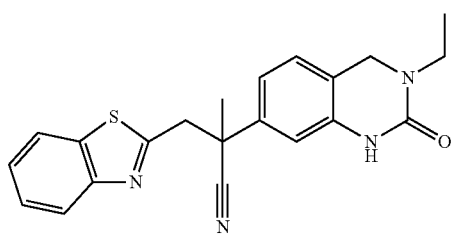
Co. No. 23; Ex. [B1];
mp. 190° C.
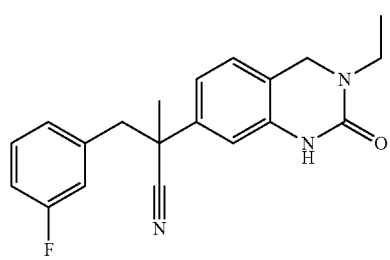
Co. No. 24; Ex. [B1];
mp. 119° C.
TABLE F-1-continued
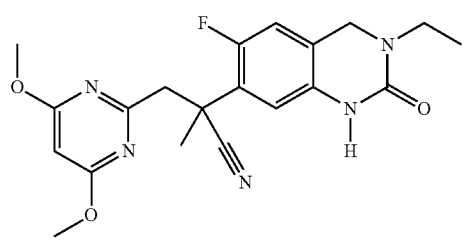
Co. No. 25; Ex. [B1];
mp. 174.5-177.0° C.
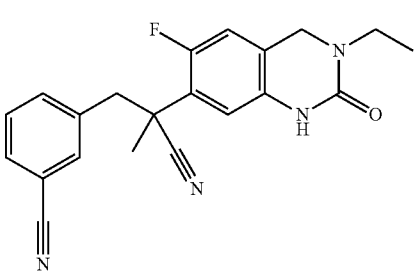
Co. No. 26; Ex. [B1];
mp. 129.0-135.0° C.
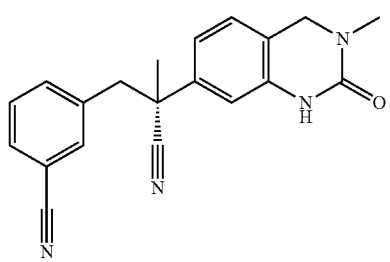
(S*); Co. No. 27; Ex. [B5];
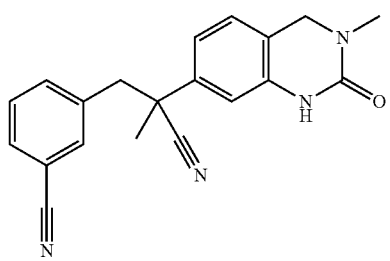
Co. No. 28; Ex. [B1]
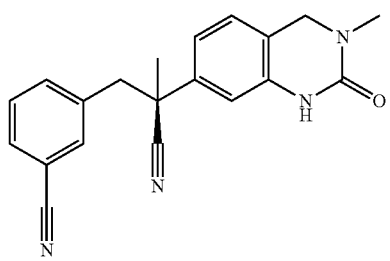
(*R); Co. No. 29; Ex. [B1]

TABLE F-1-continued

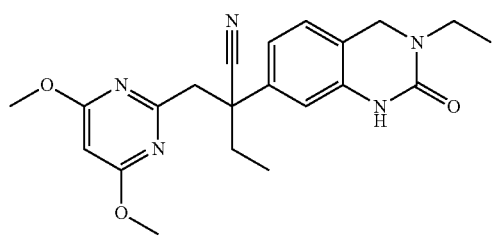

Co. No. 30; Ex. [B2];
mp. 183.0-188.0° C.

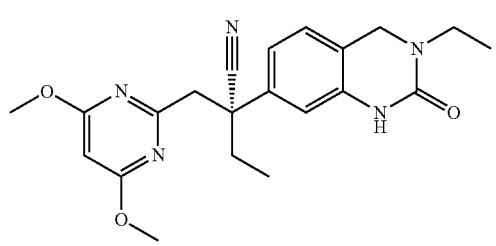

(R*); Co. No. 31; Ex. [B2]

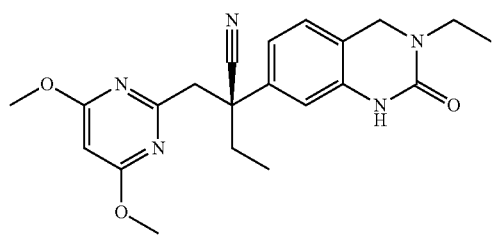

(S*); Co. No. 32; Ex. [B2]

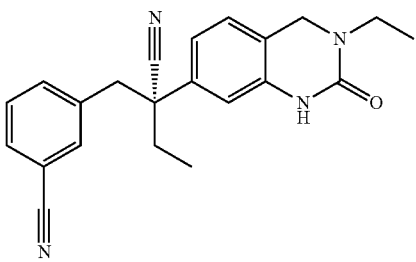

(R*); Co. No. 33; Ex. [B2]

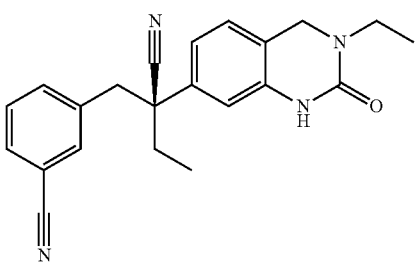

(S*); Co. No. 34; Ex. [B2].

TABLE F-1-continued

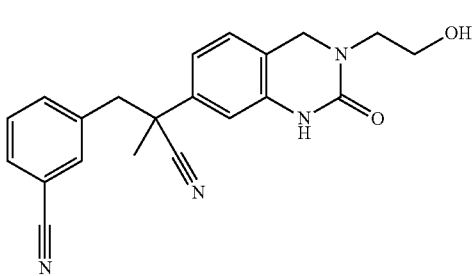

Co. No. 35; Ex. [B3];
mp. 84.0-87.0° C.

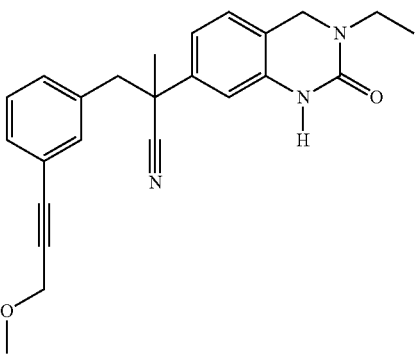

Co. No. 36; Ex. [B7]

*relative configurations

Analytical Part
LCMS
LCMS General Procedure A) The HPLC measurement was performed using an Alliance HT 2795 (Waters) system comprising a quaternary pump with degasser, an autosampler, a diode-array detector (DAD) and a column as specified in the respective methods below, the column is hold at a temperature of 30° C. Flow from the column was split to a MS spectrometer. The MS detector was configured with an electrospray ionization source. The capillary needle voltage was 3 kV and the source temperature was maintained at 100° C. on the LCT (Time of Flight Zspray™ mass spectrometer from Waters. Nitrogen was used as the nebulizer gas. Data acquisition was performed with a Waters-Micromass MassLynx-Openlynx data system.

LCMS General Procedure B
The LC measurement was performed using a UPLC (Ultra Performance Liquid Chromatography) Acquity (Waters) system comprising a binary pump with degasser, an autosampler, a diode-array detector (DAD) and a column as specified in the respective methods below, the column is hold at a temperature of 40° C. Flow from the column was brought to a MS detector. The MS detector was configured with an electrospray ionization source. The capillary needle voltage was 3 kV and the source temperature was maintained at 130° C. on the Quattro (triple quadrupole mass spectrometer from Waters). Nitrogen was used as the nebulizer gas. Data acquisition was performed with a Waters-Micromass MassLynx-Openlynx data system.

LCMS General Procedure C
The HPLC measurement was performed using an Agilent 1100 module comprising a pump, a diode-array detector (DAD) (wavelength used 220 nm), a column heater and a column as specified in the respective methods below. Flow from the column was split to a Agilent MSD Series G1946C and G1956A. MS detector was configured with API-ES (atmospheric pressure electrospray ionization). Mass spectra were acquired by scanning from 100 to 1000. The capillary needle voltage was 2500 V for positive ionization mode and 3000 V for negative ionization mode. Fragmentation voltage was 50 V. Drying gas temperature was maintained at 350° C. at a flow of 10 l/min.

LCMS-Procedure 1

In addition to the general procedure A: Reversed phase HPLC was carried out on a Xterra-MS C18 column (5 µm, 4.6×150 mm) with a flow rate of 1.0 ml/min. Two mobile phases (mobile phase A: 100% 7 mM ammonium acetate; mobile phase B: 100% acetonitrile; were employed to run a gradient condition from 85% A, 15% B (hold for 3 minutes) to 20% A, 80% B in 5 minutes, hold at 20% A and 80% B for 6 minutes and reequilibrated with initial conditions for 3 minutes. An injection volume of 20 µl was used. Cone voltage was 20 V for positive ionization mode and 20 V for negative ionization mode. Mass spectra were acquired by scanning from 100 to 900 in 0.8 seconds using an interscan delay of 0.08 seconds.

LCMS-Procedure 2

In addition to the general procedure B: Reversed phase UPLC was carried out on a Waters Acquity BEH (bridged ethylsiloxane/silica hybrid) C18 column (1.7 µm, 2.1×100 mm) with a flow rate of 0.35 ml/min. Two mobile phases (mobile phase A: 95% 7 mM ammonium acetate/5% acetonitrile; mobile phase B: 100% acetonitrile) were employed to run a gradient condition from 90% A and 10% B (hold for 0.5 minutes) to 8% A and 92% B in 3.5 minutes, hold for 2 min and back to the initial conditions in 0.5 min, hold for 1.5 minutes. An injection volume of 2 µl was used. Cone voltage was 20 V for positive and negative ionization mode. Mass spectra were acquired by scanning from 100 to 1000 in 0.2 seconds using an interscan delay of 0.1 seconds.

LCMS-Procedure 3

In addition to general procedure C: Reversed phase HPLC was carried out on a YMC-Pack ODS-AQ, 50×2.0 mm 5 µm column with a flow rate of 0.8 ml/min. Two mobile phases (mobile phase A: water with 0.1% TFA; mobile phase B: acetonitrile with 0.05% TFA) were used. First, 100% A was hold for 1 minute. Then a gradient was applied to 40% A and 60% B in 4 minutes and hold for 2.5 minutes. Typical injection volumes of 2 µl were used. Oven temperature was 50° C. (MS polarity: positive)

TABLE 2

Analytical data - Retention time ($R_t$ in minutes), (MH)$^+$ peak and LCMS procedure.

| Co. Nr. | $R_t$ | [M + H]$^+$ | LCMS Procedure |
|---|---|---|---|
| 9 | 3.30 | 316 | 3 |
| 11 | 8.71 | 374 | 1 |
| 36 | 3.63 | 388 | 2 |
| 15 | 3.44 | 375 | 2 |
| 14 | 3.54 | 381 | 2 |
| 12 | 3.32 | 374 | 2 |
| 19 | 6.62 | 380.2 | 3 |
| 28 | 5.14 | 331.2 | 3 |
| 29 | 5.2 | 331.1 | 3 |
| 27 | 5.17 | 331.1 | 3 |
| 2 | 5.43 | 359.2 | 3 |
| 31 | 5.56 | 396.1 | 3 |
| 32 | 5.57 | 396.1 | 3 |
| 33 | 5.56 | 359.1 | 3 |
| 34 | 5.57 | 359.1 | 3 |

C. Pharmacological Part

Example C.1

α-β-Tubulin Polymerization Assay

The tubulin polymerization assay is an adaptation of an assay originally described by Bonne, D. et al. (J. Biol. Chem., 1985, 260:2819-25). The assay kit was purchased from Cytoskeleton, Inc. (catalogue number BK011) and the assay was performed as described by the supplier with the following modifications. The assay was run in a 384-well black Proxiplate (Perkin Elmer) and volumes were adapted accordingly. The reactions were carried out in a final volume of 10 µl. Compounds were added to 25 µl of the reaction mix in 96-well PP plates (Corning) on ice and 10 µl of this mixture was dispensed into duplicates of the 384-well Proxiplates pre-warmed to 37° C. in a Fluoroskan Ascent plate reader (Thermo Scientific). Fluorescence measurements were taken every minute for one hour. The maximum slope of each well was determined (linear regression through 4 consecutive points) and polymerization was calculated as a percentage of polymerization observed in the absence of compound. Compounds were first measured at a concentration of 20 µM and then at 5 µM for those showing more than 50% inhibition at 20 µM as compared to the polymerization observed in the absence of compound. Results are reported in Table F-2 as scores defined as: a compound showing 0 to 50% inhibition at 20 µM is reported as score 1; a compound showing more than 50% inhibition at 5 µM is reported as score 3. Score 2 compounds are defined as compound showing more than 50% inhibition at 20 µM and less than 50% inhibition at 5 µM.

Example C.2

Eb1 Cellular Assay

The Eb1 Comet assay relies on the detection of the Eb1 protein at the plus end of polymerizing microtubules (Mimori-Kiyosue, 2000) using indirect immunofluorescence. Disruption of microtubule dynamics through de-polymerization or stabilization results in a de-localization of Eb1 from the growing microtubule ends and this is visualized by the disappearance of Eb1 containing cytoplasmic foci.

Briefly, human prostate cancer PC3 cells obtained from the American Type Culture Collection were grown in 96-well plates (Greiner, cat. no. 655090) in HAM's F12 medium as recommended by the provider (ATCC). The cells were treated for 1 hour at 37° C. with compounds dissolved in DMSO (0.6% final DMSO concentration). The culture medium was then removed by aspiration and the cells were fixed by adding cold methanol (−20° C.). After a 15 minutes incubation at −20° C., the cells were washed twice with DPBS (Gibco) containing 0.5% Triton X-100. Mouse Eb1 antibody (BD Transduction Laboratories, cat. no. 610534) was added to the cells (1/250 dilution in DPBS containing 1% BSA) and incubated overnight at room temperature. The antibody was subsequently removed and the cells washed twice with DPBS, 0.5% Triton X-100. Secondary goat anti-mouse antibody conjugated to Alexa 488 fluorescent dye (Molecular Probes) was added at a 1/500 dilution in DPBS, 1% BSA and incubated for 1 hour at 37° C. The cells were washed twice with DPBS, 0.5% Triton X-100 and then DPBS containing 0.5% Triton X-100 and 1/5000 Hoechst 33342 (Molecular Probes) was added. Microscopy based Eb1 foci visualization was carried out using an IN Cell Analyser 1000 (Amersham Biosciences) using a 20× objective. Compound dependent microtubule disruption was visually determined by the disappearance in Eb1 foci. The lowest active concentration (LAC) was determined as the concentration where Eb1 foci were absent in at least 50% of the treated cells. Herein the effects of test compounds are expressed as pLAC (the negative log value of the LAC-value) (see Table 3).

Example C.3

Detection of Anti-proliferative Effect

Human colon carcinoma HCT116 cells obtained from the ATCC were cultured in McCoy's 5A medium supplemented with 2 mM L-Glutamine, 50 µg/ml gentamicin and 10% heat inactivated fetal calf serum.

Human prostate cancer PC-3 cells obtained from the ATCC were cultured in HAM'S F12 medium supplemented with 1 mM Sodium Pyruvate, 1.5 g/L Sodium Bicarbonate, 50 µg/ml gentamicin, non-essential amino acids and 10% fetal calf serum.

Reagents Used in the Alamar Blue Assay

Resazurin was purchased from Aldrich (Prod. No. 199303). Potassium ferrocyanide, potassium ferricyanide, $KH_2PO_4$ and $K_2HPO_4$ were purchased from Sigma (Prod. Nos. P9387, P8131, P5655 and P8281, respectively).

Potassium Phosphate Buffer 0.1 M (PPB) was made as follows: 2.72 gram $KH_2PO_4$ and 13.86 gram $K_2HPO_4$ were dissolved in 500 ml milli-Q $H_2O$, the pH was adjusted to pH 7.4 and the volume was brought to 1 liter with milli-Q $H_2O$; the buffer was filter sterilised and stored at room temperature. Resazurin stock solution (PPB-A) was prepared fresh by dissolving 45 mg resazurin in 15 ml PBS. 30 mM potassium ferricyanide (PPB-B) was prepared by dissolving 0.987 gram potassium ferricyanide in 100 ml PPB. 30 mM potassium ferrocyanide (PPB-C) was prepared by dissolving 1.266 gram potassium ferrocyanide in 100 ml PPB.

Mixture of PPB-A, PPB-B and PPB-C was prepared by mixing equal volumes of the respective solutions. Resazurin work solution (herein termed "Alamar Blue" solution) was prepared by diluting said mixture 20× (vol/vol) in PPB and filter sterilising; the Alamar Blue solution could be kept at 4° C. for a maximum of 2 weeks.

Procedure of the Alamar Blue Assay

For experiments in 384 wells plates the cells were seeded at a density of $4.5 \times 10^3$ cells/ml in Falcon 384-well culture plates (Life Technologies, Merelbeke, Belgium), black with clear bottom, in 45 µl culture medium. Cells were allowed to adhere to plastic for 24 hours. The tested compound was pre-diluted (1/50 in culture medium) and 5 µl pre-diluted compound was added to the wells. Following 4-day incubation, 10 µl of the Alamar Blue solution was added to each well and the cells were further incubated for 4 hours (HCT116) or 24 hours (PC-3) at 37° C. The fluorescence intensity was measured for each well on a Fluorescence plate reader (Fluoroskan, Labsystems, 540 nm excitation and 590 nm emission)

The antiproliferative activity was calculated as percentage of remaining viable cells in treated versus control (untreated cells) conditions. Within an experiment, the result for each experimental condition is the mean of 3 replicate wells. When appropriate, the experiments were repeated to establish full concentration-response curves. When appropriate, $IC_{50}$-values (concentration of the drug, needed to reduce cell growth to 50% of the control) were computed using probit analysis for graded data (Finney, D. J., Probit Analyses, 2nd Ed. Chapter 10, Graded Responses, Cambridge University Press, Cambridge 1962). Herein the effects of test compounds are expressed as $pIC_{50}$ (the negative log value of the $IC_{50}$-value) (see Table 3).

TABLE 3

| Co. No | tubulin polymerization score | Eb1 pLAC | PC3 antiproliferative activity $pIC_{50}$ | HCT116 antiproliferative activity $pIC_{50}$ |
|---|---|---|---|---|
| 12 | | | 5.9 | 6.2 |
| 14 | | | 5.9 | 6.3 |
| 24 | | | 6.6 | 6.8 |
| 23 | | | 6.3 | 6.4 |
| 13 | | | 7.0 | 7.1 |
| 22 | | | 6.4 | 6.7 |
| 15 | | | 6.7 | 7.0 |
| 34 | 3 | 7 | 6.2 | 6.6 |
| 33 | 1 | 5.5 | <5 | <5 |
| 32 | 3 | 6.5 | 6.1 | 6.3 |
| 31 | 1 | 5.5 | <5 | <5 |
| 30 | 3 | 6.5 | 6.0 | 6.4 |
| 2 | 3 | 7 | 6.5 | 6.5 |
| 27 | 3 | 6.5 | 6.8 | 7.1 |
| 29 | | 6.5 | <5 | <5 |
| 1 | | >7.5 | 7.1 | 7.4 |
| 10 | 3 | 7 | 6.5 | 6.8 |
| 21 | 2 | 5.5 | 6.1 | 6.3 |
| 26 | 3 | 6.5 | 6.3 | 6.6 |
| 25 | 3 | 6.5 | 6.3 | 6.3 |
| 28 | 3 | 6.5 | 6.5 | 6.8 |
| 20 | | 6.5 | 6.2 | 6.4 |
| 19 | 3 | 6.5 | 6.2 | 6.4 |
| 36 | 3 | 7 | 6.6 | 6.7 |
| 11 | 3 | 7 | 6.4 | 6.5 |
| 8 | 3 | 6.5 | 6.3 | 6.7 |
| 6 | 3 | 7 | 7.0 | 7.3 |
| 5 | 1 | | <5 | <5 |
| 18 | 3 | | 6.6 | 6.6 |
| 7 | 3 | 6.5 | 6.3 | 6.1 |
| 17 | 3 | | 6.6 | 6.8 |
| 4 | 3 | | 6.3 | 6.7 |
| 3 | 1 | | <5 | <5 |
| 16 | 2 | 6 | 5.9 | 6.2 |

D. Composition Example

Film-coated Tablets

Preparation of Tablet Core

A mixture of 100 g of a compound of formula (I), 570 g lactose and 200 g starch is mixed well and thereafter humidified with a solution of 5 g sodium dodecyl sulphate and 10 g polyvinyl-pyrrolidone in about 200 ml of water. The wet powder mixture is sieved, dried and sieved again. Then there is added 100 g microcrystalline cellulose and 15 g hydrogenated vegetable oil. The whole is mixed well and compressed into tablets, giving 10.000 tablets, each comprising 10 mg of a compound of formula (I).

Coating

To a solution of 10 g methyl cellulose in 75 ml of denaturated ethanol there is added a solution of 5 g of ethyl cellulose in 150 ml of dichloromethane. Then there are added 75 ml of dichloromethane and 2.5 ml 1,2,3-propanetriol 10 g of polyethylene glycol is molten and dissolved in 75 ml of dichloromethane. The latter solution is added to the former and then there are added 2.5 g of magnesium octadecanoate, 5 g of polyvinyl-pyrrolidone and 30 ml of concentrated colour suspension and the whole is homogenated. The tablet cores are coated with the thus obtained mixture in a coating apparatus.

The invention claimed is:
1. A compound of formula (I)

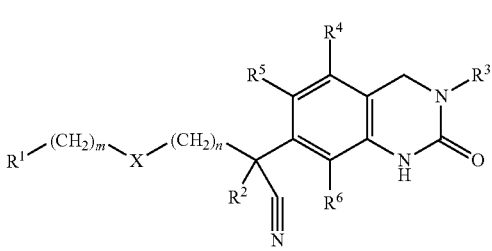

including a stereochemically isomeric form thereof;
wherein
m is 0, 1 or 2 and when m is 0 then a direct bond is intended;
n is 0, 1 or 2 and when n is 0 then a direct bond is intended;
X is a direct bond, $CR^{10}R^{11}$, $NR^8$ or O;
$R^1$ is aryl or Het;
wherein aryl is phenyl or naphthalenyl;
wherein Het is thienyl, pyrrolyl, pyrrolinyl, oxazolyl, thiazolyl, imidazolyl, pyrazolyl, isoxazolyl, isothiazolyl, oxadiazolyl, triazolyl, tetrazolyl, thiadiazolyl, furanyl, piperidinyl, pyridinyl, pyridazinyl, pyrimidinyl, piperazinyl, pyrazinyl, triazinyl, indolizinyl, azaindolizinyl, indolyl, indolinyl, benzothienyl, indazolyl, benzoxazolyl, benzimidazolyl, benzofuranyl, benzothiazolyl, benzotriazolyl, chromanyl, purinyl, quinolinyl, cinnolinyl, phthalazinyl, quinazolinyl, quinoxazolinyl, naphthyridinyl or pteridinyl;
two carbon atoms on aryl or Het can be bridged thereby forming a bi- or tricyclic moiety with a bivalent radical selected from —O—CH$_2$—CH$_2$—O— (a-1), —CH$_2$—O—CH$_2$—O— (a-2), —O—CH$_2$—CH$_2$—CH$_2$— (a-3), —O—CH$_2$—CH$_2$—NR$^8$— (a-4), —O—CR$^8_2$—O— (a-5), —O—CH$_2$—CH$_2$— (a-6), —CH$_2$—N—CH$_2$—CH$_2$— (a-7), —(CH$_2$)$_3$— (a-8), or —(CH$_2$)$_4$— (a-9);

each aryl, Het, bridged aryl or bridged Het can be substituted with one, two, three, four or five substituents each independently selected from halo, cyano, nitro, hydroxycarbonyl, $C_{1-6}$alkyl, $C_{2-6}$alkenyl, $C_{2-6}$alkynyl, $C_{3-6}$cycloalkyl,
amino $C_{3-6}$cycloalkyl, halo$C_{1-6}$alkyl, trihalo$C_{1-6}$alkyl, $C_{1-6}$alkylcarbonyl, $C_{1-6}$alkyloxycarbonyl, $C_{2-6}$alkenylcarbonyl, oxime, $C_{1-6}$alkyloxime, amidoxime, —C≡C—CH$_2$O—CH$_3$, —C≡C—CH$_2$N(CH$_3$)$_2$, —C≡C—Si(CH$_3$)$_3$, hydroxy$C_{1-6}$alkyl, hydroxy$C_{2-6}$alkenyl, hydroxy$C_{2-6}$alkynyl, cyano$C_{1-6}$alkyl, cyano $C_{2-6}$alkenyl, aminocarbonyl$C_{1-6}$alkyl, $C_{1-6}$alkylsulfonyl$C_{1-6}$alkyl, $C_{1-6}$alkylsulfonyl$C_{2-6}$alkenyl, $C_{1-6}$alkylsulfonyl$C_{2-6}$alkynyl, -PO(O$C_{1-6}$alkyl)$_2$, —B(OH)$_2$, —S—CH$_3$, SF$_5$, $C_{1-6}$alkylsulfonyl, —NR$^8$R$^9$, —$C_{1-6}$alkylNR$^8$R$^9$, —OR$^8$, —$C_{1-6}$alkylOR$^8$, —CONR$^8$R$^9$, piperidinyl$C_{1-6}$alkyl, piperazinyl$C_{1-6}$alkyl, $C_{1-6}$alkylpiperazinyl$C_{1-6}$alkyl, morpholinyl$C_{1-6}$alkyl, piperidinyl, piperazinyl, $C_{1-6}$alkylpiperazinyl, morpholinyl, phenyl, thienyl, pyrazolyl, pyrrolyl, pyrrolidinyl, pyridinyl, pyrimidinyl, oxadiazolyl, imidazolyl, imidazolyl$C_{2-6}$alkynyl, $C_{1-6}$alkylimidazolyl$C_{2-6}$alkynyl, cyanopyridinyl, phenyl$C_{1-6}$alkyl, phenyl$C_{2-6}$alkenyl, $C_{1-6}$alkyloxyphenyl,
trihalo$C_{1-6}$alkylphenyl, methylpyrazolyl, halopyrimidinyl or dimethylaminopyrrolidinyl;
$R^2$ is hydrogen, methyl, ethyl, propyl, $C_{3-6}$cycloalkyl, $C_{3-6}$cycloalkylmethyl, fluor, phenyl, cyanophenyl or trifluoromethyl;
$R^3$ is methyl, ethyl, propyl, hydroxymethyl, hydroxyethyl, halo, trifluoromethyl, methyloxy or $C_{1-6}$alkylcarbonyl;
each $R^4$, $R^5$ and $R^6$ is independently selected from hydrogen, halo, $C_{1-6}$alkyloxy, cyano, $C_{1-6}$alkyl, —OCH$_2$CH$_2$NR$^8$R$^9$, —CH$_2$OCH$_2$CH$_2$NR$^8$R$^9$, —OCH$_2$CH$_2$CH$_2$NR$^8$R$^9$ or $C_{1-6}$alkyloxy$C_{1-6}$alkyloxy;
each $R^8$ and $R^9$ is independently selected from hydrogen, halo, $C_{1-6}$alkyl, $C_{2-6}$alkenyl, $C_{2-6}$alkynyl, carbonyl, $C_{1-6}$alkylsulfonyl$C_{1-6}$alkyl,
$C_{1-6}$alkyloxy$C_{1-6}$alkyl, hydroxy$C_{1-6}$alkyl, dihydroxy$C_{1-6}$alkyl, cyano$C_{1-6}$alkyl, trihalo$C_{1-6}$alkyl, phenyl$C_{1-6}$alkyl, (di$C_{1-6}$ alkyl)amino$C_{1-6}$alkyl, $C_{1-6}$alkylsulfonyl, morpholinyl$C_{1-6}$alkyl, morpholinylcarbonyl, piperazinyl$C_{1-6}$alkyl,
$C_{1-6}$alkylpiperazinyl$C_{1-6}$alkyl, piperidinyl$C_{1-6}$alkyl, thiomorpholinyl$C_{1-6}$alkyl, $C_{3-6}$cycloalkylmethyl, pyridinyl, pyrimidinyl, phenyl, halophenyl, oxanyl$C_{1-6}$alkyl, $C_{1-6}$alkylsulfonyl$C_{1-6}$alkyl or $C_{1-6}$alkylcarbonylamino$C_{1-6}$alkyl;
each $R^{10}$ and $R^{11}$ is independently selected from hydrogen, methyl, hydroxyl; or $R^{10}$ and $R^{11}$ are taken together with the carbon atom to which they are attached to form a cyclopropyl ring or a radical of formula C(=O);
a N-oxide form thereof, or a pharmaceutically acceptable addition salt thereof.

2. A compound as claimed in claim 1 wherein
m is 0 or 1; $R^1$ is phenyl or Het; wherein Het is pyridinyl, pyrimidinyl or benzothiazolyl; two carbon atoms on Het can be bridged with the bivalent radical (a-8); each phenyl or Het or bridged Het can be substituted with one or two substituents each independently selected from halo, cyano, $C_{1-6}$alkyl, $C_{2-6}$alkynyl,
—C≡C—CH$_2$O—CH$_3$, hydroxy$C_{2-6}$alkynyl or —OR$^8$; $R^2$ is methyl or ethyl; $R^3$ is methyl, ethyl or hydroxyethyl; each $R^4$, $R^5$ and $R^6$ is independently selected from hydrogen or halo; each $R^8$ is hydrogen or $C_{1-6}$alkyl; and each $R^{10}$ and $R^{11}$ is hydrogen.

3. A compound as claimed in claim 1 wherein
m is 0 and n is 0; X is a direct bond or CH$_2$; $R^1$ is phenyl, pyridinyl or pyrimidinyl; when $R^1$ is pyridinyl two carbon atoms on the pyridinyl can be bridged with the bivalent radical (a-8); each phenyl, pyridinyl or pyrimidinyl can be substituted with one or two substituents each independently selected from halo, cyano or $C_{1-6}$alkyloxy; $R^2$ is methyl; $R^3$ is methyl or ethyl; and each $R^4$, $R^5$ and $R^6$ is hydrogen.

4. A compound as claimed in claim 1 wherein $R^3$ is methyl, ethyl, propyl, hydroxymethyl, halo, trifluoromethyl, methyloxy or $C_{1-6}$alkylcarbonyl.

5. A compound as claimed in claim 1 which is selected from the following:

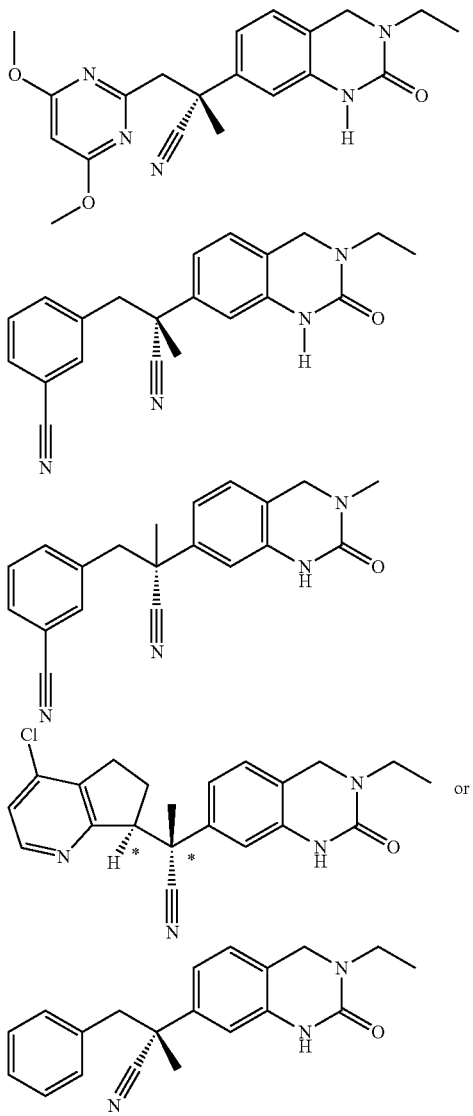

wherein the asterisk (*) indicates relative configuration;
or a pharmaceutically acceptable addition salt thereof.

6. A pharmaceutical composition comprising a compound claimed in claim 1 in a pharmaceutically acceptable carrier.

7. A composition of claim 6 comprising the combination with another anticancer agent chosen from the group consisting of cisplatin optionally combined with amifostine, carboplatin or oxaliplatin; paclitaxel, paclitaxel protein bound particles, Abraxane™, or docetaxel; camptothecin compounds; etoposide, etoposide phosphate or teniposide; vinblastine, vincristine or vinorelbine; 5-fluorouracil, leucovorin, gemcitabine, gemcitabine hcl, capecitabine, cladribine, fludarabine, nelarabine; cyclophosphamide, chlorambucil, carmustine, thiotepa, mephalan (melphalan), lomustine, altretamine, busulfan, dacarbazine, estramustine, ifosfamide optionally in combination with mesna, pipobroman, procarbazine, streptozocin, telozolomide, uracil; daunorubicin, doxorubicin optionally in combination with dexrazoxane, doxil, idarubicin, mitoxantrone, epirubicin, epirubicin hcl, valrubicin; picropodophilin; tetrocarcin A; prednisone; trastuzumab (HER2 antibody), rituximab (CD20 antibody), gemtuzumab, gemtuzumab ozogamicin, cetuximab, pertuzumab, bevacizumab, alemtuzumab, eculizumab, ibritumomab tiuxetan, nofetumomab, panitumumab, tositumomab, CNTO 328; tamoxifen, fulvestrant, toremifene, droloxifene, faslodex, raloxifene or letrozole; exemestane, anastrozole, letrazole, testolactone and vorozole; retinoids, vitamin D or retinoic acid and accutane; azacytidine or decitabine; premetrexed disodium; antinomycin D, bleomycin, mitomycin C, dactinomycin, carminomycin, daunomycin, levamisole, plicamycin, mithramycin; clofarabine, aminopterin, cytosine arabinoside or methotrexate, azacitidine, cytarabine, floxuridine, pentostatin, thioguanine; apoptosis inducing agents and antiangio egents; combrestatin, colchicines or nocodazole; flavoperidol, imatinib mesylate, erlotinib, gefitinib, dasatinib, lapatinib, lapatinib ditosylate, sorafenib, sunitinib, sunitinib maleate, temsirolimus; tipifarnib; sodium butyrate, suberoylanilide hydroxamide acid, depsipeptide, NVP-LAQ824, R306465, JNJ-26481585, trichostatin A, vorinostat; PS-341, MLN .41 or bortezomib; yondelis; telomestatin; batimastat, marimastat, prinostat or metastat; aldesleukin, denileukin diftitox, interferon alfa 2a, interferon alfa 2b, peginterferon alfa 2b; MAPK inhibitors; alitretinoin, bexarotene, tretinoin; arsenic trioxide; asparaginase; dromostanolone propionate, megestrol acetate, nandrolone decanoate, or phenpropionate; dexamethasone; abarelix, goserelin acetate, histrelin acetate, leuprolide acetate; thalidomide, lenalidomide; mercaptopurine, mitotane, pamidronate, pegademase, pegaspargase, rasburicase; ABT-737; PD98059, AZD6244, CI-1040; filgrastim, pegfilgrastim, sargramostim; erythropoietin or darbepoetin alfa; interleukin 11; oprelvekin; zoledronate, zoledronic acid; fentanyl; bisphosphonate; and palifermin.

* * * * *